United States Patent [19]

Foss et al.

[11] Patent Number: 5,266,651
[45] Date of Patent: Nov. 30, 1993

[54] CROSSLINKED POLED POLYMERS FOR NONLINEAR OPTIC APPLICATIONS AND METHOD OF MAKING THEM

[75] Inventors: Robert P. Foss, Hockessin, Del.; Wilson Tam, Boothwyn, Pa.; Fredrick C. Zumsteg, Jr., Wilmington, Del.

[73] Assignee: E. I. Du Pont de Nemours and Company, Wilmington, Del.

[21] Appl. No.: 695,379

[22] Filed: May 3, 1991

[51] Int. Cl.$^5$ .................. C08F 230/08; C08F 224/00; C08F 222/22

[52] U.S. Cl. .................. 525/326.5; 525/327.3; 525/327.4; 525/327.5; 525/327.6; 525/328.2; 525/329.7; 525/329.8; 525/329.9; 525/330.3; 525/330.4; 525/330.5; 525/333.3; 525/333.5; 525/333.6; 525/276; 525/353; 525/376; 525/377; 525/351; 525/348

[58] Field of Search .................. 525/328.2, 377, 327.3, 525/348, 351, 353, 376, 326.5, 329.7, 329.8, 329.9, 330.3, 330.4, 330.5, 326.5

[56] References Cited

U.S. PATENT DOCUMENTS

| | | | |
|---|---|---|---|
| 3,475,388 | 10/1969 | Yocum | 525/377 |
| 4,771,112 | 9/1988 | Engelbrecht | 525/327.3 |
| 4,962,163 | 10/1990 | Hefner et al. | 525/463 |
| 5,030,697 | 7/1991 | Hugl et al. | 525/326.9 |

FOREIGN PATENT DOCUMENTS

| | | |
|---|---|---|
| 0394027 | 10/1990 | European Pat. Off. . |
| 492527 | 1/1976 | U.S.S.R. . |
| WO9108198 | 6/1991 | World Int. Prop. O. . |

OTHER PUBLICATIONS

H. Lee & K. Neville, Handbook of Epoxy Resins, McGraw-Hill, New York, 1967, 2-10 to 2-11.
Niyes Data Corp., Epoxy Resin Handbook, 1972, p. 174.
L-T Cheng et al. (1989) *SPIE 1147*, 61-72.
Chem. Abstr. 100 (14): 103994q [Eur. Polym. J. 19(12), 1107-12 (1983); C. Crepeau et al.].
Chem. Abstr. 94 (12): 85909s [Fuji Film Co. JP-5-5-139471 (1980) Kokai].
Williams D. J. (1984) Angew. Chem. Int. Ed. Engl. 23, 690-703.
Wagener et al., Polymer Preprints, vol. 32, No. 1, Mar. 1991, American Chemical Society, pp. 623-624.
Feiring et al., Journal of Polymer Science: Part A: Polymer Chemistry, vol. 28, No. 8, Jul. 1990, New York, pp. 2809-2819.
Eich et al., J. Appl. Phys. 66(7), Oct. 1, 1989, pp. 3241-3247.
Hubbard et al., Chemistry of Materials, vol. 1, No. 2, Mar./Apr. 1989, pp. 167-169.

*Primary Examiner*—Joseph L. Schofer
*Assistant Examiner*—Mark Nagumo
*Attorney, Agent, or Firm*—R. Thomas Gallegos

[57] ABSTRACT

Polymer reagents containing reactive functional groups are crosslinked by reacting them with compounds (crosslinking agents) which contain complimentary functional groups and have large nonlinear polarizability. The resulting polymer reagents, after poling, are useful for nonlinear optic applications. Also disclosed are the mixture which react to form the crosslinked polymer and novel crosslinking agents.

61 Claims, No Drawings

CROSSLINKED POLED POLYMERS FOR NONLINEAR OPTIC APPLICATIONS AND METHOD OF MAKING THEM

BACKGROUND OF THE INVENTION

Organic molecules having large nonlinear polarizabilities have been recognized as potentially useful as components of the optical elements in optical frequency converters and in electrooptic devices. In order to create organic materials exhibiting the large second order optical susceptibilities essential to nonlinear optic applications, the molecules must be constructively arrayed in a noncentrosymmetric configuration. Such molecules have been crystallized in a noncentrosymmetric space group, but this method does not work for all potentially useful molecules and the resulting shape and properties are limited by the very nature of a crystal.

A number of other methods for noncentrosymmetrically arranging the molecules to optimize the nonlinear properties of the resulting organic material have been used. For example, strong DC electric poling fields have been applied to polar dye molecules in semi-fluid polymeric or glassy matrices in order to align the molecules noncentrosymmetrically. The matrices are then rigidified, while still under the influence of the externally applied DC field, to "lock" the at least partially aligned dye molecules in place. In still another approach polar dyes are attached directly to polymeric backbones which are similarly treated to lock the polar dyes in biased alignment. These methods have had limited success, because the polymer matrix allows the molecules therein to "relax" over time thereby losing the configuration necessary for the enhanced nonlinear optic properties. Furthermore, the polymer can dilute the effective nonlinearity, as it is often difficult to get more than 10 to 20 percent of nonlinear molecules into the polymer reagent.

One of the more promising and recent approaches to making stable nonlinear optically active organic materials involves forming highly crosslinked networks where polar molecules (e.g., dyes) are polymerized directly into the polymer reagent matrix during the poling process. Eich et al., J. Appl. Phys. 66(7), Oct. 1, 1989, pp.3241-3247, discloses the preparation of nonlinear optically active crosslinked polymer networks from the reaction of diepoxides, with and without nonlinear optic (NLO) dye moieties, and NLO active di- and tri-functional amines. Hubbard et al., Chemistry of Materials, Volume 1, Number 2, March/April, 1989, pp. 167-169, disclose crosslinked epoxy polymer reagent networks containing dispersed NLO dyes similar to those disclosed by Eich et al. While these epoxide networks provide significantly improved thermal stability of NLO properties relative to earlier polymeric systems, preparation of the epoxide networks require complex processing steps to avoid interruption of the poling process by excessive conductivity.

This invention avoids the processing problems associated with conventional crosslinked polymer networks by forming the network from a mixture of a preformed reactive polymer reagent and a monomeric crosslinking agent, at least part of which contains a dye.

SUMMARY OF THE INVENTION

This invention concerns a crosslinked polymer, comprising, the product of the reaction of:

(a) a polymer reagent having a degree of polymerization of at least 3, and 2 or more active groups; and (b) a crosslinking agent containing one or more dye moieties and two or more reactive groups;

wherein at least one of the polymer reagent or crosslinking agent has three or more active or reactive groups, respectively.

This invention also concerns a mixture, comprising, (a) a polymer reagent having a degree of polymerization of at least 3, and 2 or more active groups; and (b) a crosslinking agent containing one or more dye moieties and two or more reactive groups;

wherein at least one of the polymer reagent or crosslinking agent has three or more active or reactive groups, respectively.

This invention also concerns a process for producing a nonlinear optical element, comprising, crosslinking while simultaneously applying an electric field to, a mixture of:

(a) a polymer reagent having a degree of polymerization of at least 3, and 2 or more active groups; and (b) a crosslinking agent containing one or more dye moieties and two or more reactive groups;

wherein at least one of the polymer reagent or crosslinking agent has three or more active or reactive groups, respectively.

This invention also concerns novel compounds useful as crosslinking agents for making crosslinked poled polymers having nonlinear optic applications.

DETAILED DESCRIPTION OF THE INVENTION

This invention involves two compositions, a mixture and a crosslinked polymer which is made from the mixture, and a process for producing a nonlinear optical element from the mixture. All of the embodiments and preferred embodiments described below for the composition of the mixture are also applicable to the crosslinked polymer and the process.

The mixture comprises a polymer reagent and a crosslinking agent which can react with each other to form a crosslinked polymer. In order to form a crosslinked polymer, the polymer reagent and crosslinking agent must contain groups that are complimentary to each other, that is can react with each other to form the crosslinked polymer. For the sake of clarity, such groups attached to the polymer reagent will be referred to as "active groups" herein, and such groups attached to the crosslinking agent will be referred to as "reactive groups" herein.

More than one type of active group and/or reactive group may be present in the mixture, but if this is the case, each of the active groups must not react with any of the other active groups, and each of the reactive groups must not react with any of the other reactive groups. However, as mentioned above, the active and reactive groups should react with each other. Typical complimentary groups are shown in the two columns below, the groups in column (b) being complimentary to those in column (a).

| (a) | (b) |
|---|---|
| epoxy | amino[1], hydroxyl, carboxyl |

-continued

| (a) | (b) |
|---|---|
| isocyanate | amino[1], hydroxyl, thiol |
| acyl halide | amino[1], hydroxy |
| carboxyl anhydride | amino[1], hydroxy |
| alkoxysilyl | alkoxysilyl[2], silanol |
| aziridinyl | amino, carboxyl, aromatic hydroxyl |

[1] Primary and secondary amino only.
[2] Water needed for the reaction of these groups.

In order to pick a set of complimentary active and reactive groups, one would choose a group from column (a) and a group from column (b), on the same line. The choice of active and reactive groups from columns (a) and (b) would depend primarily upon the availability or difficulty in synthesizing the particular polymer reagent and crosslinking agent with those groups. Useful examples of compounds having complementary groups are described below. It is preferred if the active and reactive groups are chosen so that when they react no small molecules are produced. For example, hydrolysis and condensation of the alkoxysilyl groups will produce an alcohol, which is undesirable, but reaction of an isocyanate with an amino group produces no small molecule. Preferred active or reactive groups are epoxy and isocyanate and their complimentary groups, and an especially preferred active or reactive group is isocyanate.

It is believed that, consistent with other desired properties (such as low brittleness), the higher the functionality of the polymer reagent and/or crosslinking agent, the more optically stable will be the poled crosslinked polymer. It is particularly preferred if the polymer reagent has at least about one active group for each three monomeric units, and especially preferred if it has at least about one active group for each two monomer units. Polymer reagents with only two active groups per molecule may be used, so long as the crosslinking agent contains at least three reactive groups. If the crosslinking agent contains two reactive groups, the polymer reagent should contain three or more active groups. If the polymer reagent contains only two active groups, it is preferred if the active groups are end groups.

The polymer reagent used in the present invention has a degree of polymerization of at least 3. By degree of polymerization is meant the average number of monomer units in a polymer reagent molecule. Although there is no upper limit on the degree of polymerization from a theoretical standpoint, practical considerations, such as the ability to form shapes and mix the polymer reagent with the crosslinking agent, dictate preferred upper limits on the degree of polymerization. Conversely, the lower limit on the degree of polymerization is dictated by the desire to have a mixture whose viscosity is higher than that of similar monomeric compounds (see below for the reason), while being as low in viscosity as possible in order to mix the ingredients and form a shape. Therefore it is preferred if the degree of polymerization is 5 to about 300, and more preferred if the degree of polymerization is about 10 to about 200.

The polymer reagent contains two or more active groups. The active groups may have been present in some or all of the monomers used to form the polymer reagent, or may be formed on the polymer reagent by chemical modification after the monomers have been polymerized. An active group is defined as a group that will react with one reactive group on the crosslinking agent. An active group may react with "X" (a number) reactive groups, in which case such a active group would count as X active groups. For example, a primary amine may react with two epoxy groups, in which case the primary amine would count as two active groups.

The polymer reagent may be formed from appropriate monomers by methods well known to those skilled in the art, for example addition or condensation polymerization. Addition polymers, particularly vinyl addition polymers, are preferred, since reactive groups are relatively easy to introduce into such polymers as part of the monomer units. The polymers may be homopolymers or copolymers. It is preferred that the monomers be chosen so that the resulting crosslinked polymer does not contain a substantial crystalline fraction, i.e., is amorphous. A minor amount of crystallinity can be tolerated without loss of desirable nonlinear optical properties. In general, the presence of significant crystallinity in the crosslinked polymer can cause a reduction in efficiency. For example, crystallinity can cause increased scattering of the incident radiation, which can significantly decrease the efficiency of any optical device utilizing these crosslinked polymers. Furthermore, depending on the amount, location and type of crystallinity in the crosslinked polymer, SHG (second harmonic generation) can be greatly diminished. If the polymer reagents are copolymers, not all of the monomeric units need contain active groups, although it is preferred if as high a proportion as possible do. This high proportion of active groups is desirable because a relatively high proportion of dye moiety containing crosslinking agent may be used, which contributes to strong nonlinear optical properties. Counterbalancing this desirable property is the effect of high crosslink density on such compositions, such as brittleness. Such compromises are familiar to one skilled in the art, and methods of developing optimum properties are known and require a minimum of experimentation. Thus crosslink density may be lowered by using a higher proportion of monomer units that do not contain active groups.

Preferred vinylic monomers from which the polymer reagent is made include acrylic monomers and styrene and substituted styrenes. Particularly preferred acrylic monomers are methacrylates, which give polymer reagents with higher glass transition temperatures, which is believed to be advantageous for the stability of the NLO effect. Monomers containing functional groups which are useful in the polymer reagent, include but are not limited to, maleic anhydride, acryloyl chloride, methacryloyl chloride, 2-isocyanatoethyl methacrylate, glycidyl methacrylate, glycidyl acrylate, 4-isocyanatostyrene, 3-(2-isocyanato-2-propyl)-α-methylstyrene, 2-hydroxyethyl methacrylate, 4-aminostyrene, methyacrylic acid, and 3-trimethoxysilylpropyl methacrylate. Preferred functional monomers are acryloyl chloride, methacryloyl chloride, 2-isocyanatoethyl methacrylate, glycidyl methacrylate, glycidyl acrylate 4-isocyanatostyrene and 3-(1-isocyanato-2-propyl)-α-methylstyrene. Monomers not containing functional groups include, but are not limited to, methyl methacrylate, styrene, 4-methylstyrene, cyclohexyl methacrylate, ethyl acrylate, and phenyl methacrylate. Preferred nonfunctional monomers are methyl methacrylate and styrene.

The monomeric crosslinking agent used in the present invention has two general structural features - it contains at least two reactive groups and a dye moiety. The nature of the reactive groups is discussed above. A reactive group may react "X" (a number) active groups, in which case such a reactive group would count as X active groups. For example, a primary amine may react with two epoxy groups, in which case the primary amine would count as two reactive groups.

The dye moiety useful in the practice of this invention should have a molecular hyperpolarizability, beta, of greater than about $10^{-30}$ esu (electrostatic units) measured by conventional EFISH methods, as described in L. T. Cheng, et al., SPIE, vol. 1147, p. 61–72 (1989) which is incorporated herein by reference. Dye moieties often have three subunits, arranged A-E-D. A is an electron acceptor group such as cyano, nitro, perfluoroalkylsulfonyl, D is an electron donor group such as amino or alkoxy, and E is a group having a conjugated pi bond system. These groups are arranged within the dye moiety so that it has noncentrosymmetric molecular dipoles having an electron donor group linked through a pi-bonding system to an electron acceptor group. Such dye moieties (either as compounds in their own right, or as parts of compounds), and their structural requirements, are well known to those skilled in the art, see for example L. T. Cheng, et al., supra. Examples of crosslinking agents useful herein include, but are not limited to, [4-(2-hydroxymethyl-1-pyrrolidinyl)-phenyl][1,1-difluoro-2-hydroxy-2-phenylethyl]sulfone, 3,3'-bis(hydroxymethyl)-4-N,N-dimethylamino-4'-nitro-trans-stilbene, 3,4-diamino-nitrobenzene, 3,4-dihydroxynitrobenzene, 4-bis(2-hydroxyethyl)aminonitrobenzene, 3-hydroxy-4-aminonitrobenzene, Disperse Red 19, 1-[N,N-bis(2-hydroxyethyl)amino]-4-(2,2-dicyanoethenyl)benzene and a compound of the formula:

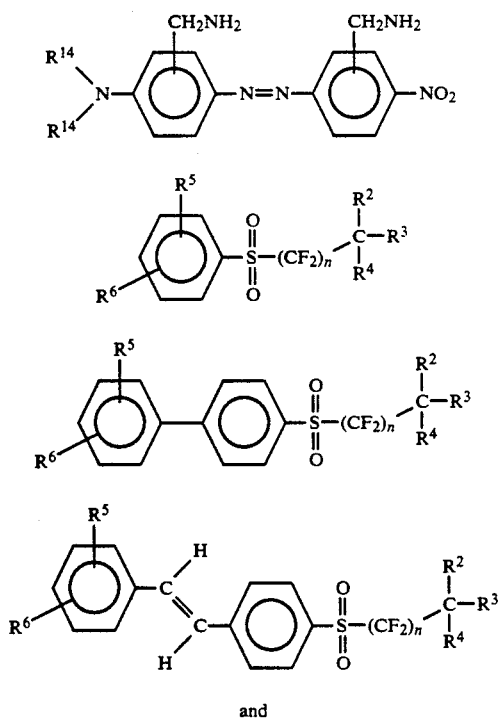

and

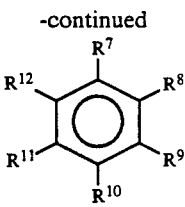

wherein:

$R^2$, $R^3$, $R^4$, $R^5$, and $R^6$ are independently selected from the group consisting of hydrogen, hydroxyl, amino, $-OR^{13}$, $-NHR^{13}$, hydroxyl or primary or secondary amino substituted hydrocarbyl of 1–20 carbon atoms, hydroxyl or primary or secondary amino substituted heterocyclic rings containing 3–6 carbon atoms, hydrocarbyl and heterocyclic rings containing 3–6 carbon atoms;

$R^{13}$ is hydroxyl or primary or secondary amino substituted hydrocarbyl of 1–20 carbon atoms, hydroxyl or primary or secondary amino substituted heterocyclic rings containing 3–6 carbon atoms, hydrocarbyl and heterocyclic rings containing 3–6 carbon atoms;

$R^7$, $R^8$, $R^9$, $R^{10}$, $R^{11}$, and $R^{12}$ are independently selected from the group Consisting of hydrogen, hydroxyl, amino, $-OR^{13}$, $-NHR^{13}$, hydroxyl or primary or secondary amino substituted hydrocarbyl of 1–20 carbon atoms, hydroxyl or primary or secondary amino substituted heterocyclic rings containing 3–6 carbon atoms, hydrocarbyl and heterocyclic rings containing 3–6 carbon atoms;

$R^{14}$ is hydrocarbyl containing 1–20 carbon atoms;

n is an integer from 1 to 20; and provided that at least two of $R^2$, $R^3$, $R^4$, $R^5$, $R^6$, $R^7$, $R^8$, $R^9$, $R^{10}$, $R^{11}$, $R^{12}$, and $R^{13}$ must be hydroxyl, amino, $-OR^{13}$, $-NHR^3$, hydroxyl or primary or secondary amino substituted hydrocarbyl of 1–20 carbon atoms, hydroxyl or primary or secondary amino substituted heterocyclic rings containing 3–6 carbon atoms.

Preferred crosslinking agents are a compound of the formula

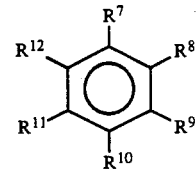

wherein:

at least two of $R^7$, $R^8$, $R^9$, $R^{10}$, $R^{11}$, and $R^{12}$ are independently selected from the group consisting of hydroxyl and amino, and one of $R^7$, $R^8$, $R^9$, $R^{10}$, $R^{11}$, and $R^{12}$ is nitro; Disperse Red 19, 1-[N,N-bis(2-hydroxyethyl)amino]-4-(2,2-dicyanoethenyl)benzene, [4-(2-hydroxymethyl-1-pyrrolydinyl)phenyl][1,1,2,2,3,3,4,4-octafluoro-5-methyl-5-hydroxyhexyl]sulfone; and [4-(2-hydroxymethyl-1-pyrrolidinyl)phenyl][1,1-difluoro-2-hydroxy-2-phenylethyl]sulfone. Especially preferred crosslinking agents are 1-[N,N-bis(2-hydroxyethyl)amino]-4-(2,2-dicyanoethenyl)benzene, 3,4-diaminonitrobenzene, 3-hydroxy-4-aminonitrobenzene, Disperse Red 19, [4-(2-hydroxymethyl-1-pyrroly-dinyl)-phenyl][1,1,2,2,3,3,4,4-octafluoro-5-methyl-5-hydroxyhexyl]sulfone; and [4-(2-hydroxymethyl-1-pyrrolidinyl)phenyl][1,1-difluoro-2-hydroxy-2-phenylethyl]sulfone.

The two components of the mixture, the polymer reagent and crosslinking agent, may be mixed by conventional means, e.g., stirring to mix two liquids or dissolving one solid in a liquid. Heat may be used if necessary to effect the mixing, however, care must be taken to avoid much reaction until a homogeneous mixture (solution) is obtained. The reactivity can be adjusted by the selection of the active and reactive groups, and the molecules which they are part of. If reaction is slow, a catalyst for the reaction may be added, provided it does not substantially affect the properties of the mixture or the resulting crosslinked polymer. Such catalysts are well known to those skilled in the art for various active and reactive groups, including those enumerated above, and the chemical reactions involved are also well known to those skilled in the art. The resulting crosslinked polymer is useful as a film, but the film must be formed before substantial crosslinking reaction takes place.

The mixture described herein is used to produce a crosslinked polymer in which a substantial proportion of the dye moieties are in biased alignment resulting in a crosslinked polymer having desirable nonlinear optical properties. Simultaneous with crosslinking, an electrical field may be applied. While the mixture is in a low viscosity state, i.e., prior to significant crosslinking, a substantial proportion of the molecular dipoles in the dye moieties align in response to the electrical field, and then, upon increasing the viscosity by continued crosslinking, the rotational freedom of the dye moieties is decreased to an extent that they are substantially locked in biased alignment. Such a process is often referred to as poling. The crosslinked polymer of the present invention is referred to herein as a crosslinked poled polymer. About the time the crosslinking is completed or at least highly advanced, the electric field can be removed, and the dye moieties will retain their alignment, resulting in a relatively stable poled crosslinked polymer useful as a nonlinear optical element, or a component thereof. Methods of controlling the reaction rate are described above and illustrated in the Examples. If the mixture of the polymer reagent and the crosslinking agent is a glass, it is preferable that the mixture be above its glass transition temperature (Tg) to afford good mobility of the dye moieties.

An electric field for poling is commonly created in one of two ways, corona poling or electrode poling.

In electrode poling the electric field is created between two closely spaced electrodes. Depending on the desired sample configuration, these electrodes can either be in the plane of a thin film, in which case the field is primarily parallel to the surface of the sample; or it can be in a plane above and below the sample, in which case the field is perpendicular to the sample surface. The latter configuration has the advantage of generating high fields over a large area, but has the disadvantage for frequency doubling of requiring that the electrodes are transparent (transparency required only to measure transmitted SHG light) and that the sample is tilted with respect to the input beam. This latter requirement is necessary so that a component of the fundamental beam's electric field can be parallel to the poling direction.

Electrode poling has several disadvantages, particularly when surveying a large number of new materials where the thin film quality and characteristics have not been optimized. Because of the high fields involved, electrochemistry can take place at the electrodes, thereby altering material properties. Also microscopic defects can lead to electrical breakdown at potentials many times smaller than a defect-free film could sustain. Such a breakdown will typically ruin a sample since the entire charge contained on the electrodes will flow through a small area of the sample causing thermal damage not only to the sample but also to the electrodes.

Corona poling avoids these disadvantages. A corona discharge is used to create the electric field by depositing charge on a thin film sample which has been coated on a conductive substrate. Corona poling eliminates the high voltage electrode. Since there is no conductive electrode to carry charge to a defect, the catastrophic damage associated with having a conductive point defect is also eliminated. This technique does, however, have the limitations of requiring a transparent (transparency required only to measure transmitted SHG light) electrode and a tilted sample. In addition, since a corona discharge is a current limited source, modest sample conductivity will cause a reduction in the maximum field which can be generated. For a discussion of corona poling, see, e.g., K. D. Singer et al., "Electro-optic phase modulation and optical second harmonic generation in corona-poled polymer films", Appl Phys. Lett. 53(19) pp. 1800–1802 (1988).

A preferred form of nonlinear optical element is a film. Nonlinear optical films can be produced by spin coating e.g., depositing a solution of the mixture on the center of rotation of a usually flat substrate, whereby the solution spreads out over the substrate, and the solvent is evaporated, leaving the mixture in the form of a film, and then poling and crosslinking the spin coated film.

The crosslinked poled polymers of this invention are considered particularly useful because of their high concentration of nonlinear optically active molecules, their capability of being formed into large area thin films, and their high orientational stability. Preferred film thickness can vary according to use. Typically film thickness is within the range of 0.5 $\mu$m–2 $\mu$m.

Crosslinked poled polymers can be provided in other forms as well (e.g., a solid block of polymer could be formed into an electrooptic modulator or a frequency converter using conventional techniques known in the art for single crystals) and poled polymers in other forms are also included within this invention.

The crosslinked poled polymers of this invention are preferably shaped to function as nonlinear optical elements for transforming electromagnetic radiation (e.g., by changing the frequency and/or polarization of the radiation). Generally, the nonlinear optical element of a crosslinked poled polymer is used for transforming electromagnetic radiation by including it within an optical device. A device for transforming electromagnetic radiation using a nonlinear optical element is described in U.S. Pat. No. 4,909,964. The present invention may be used in such a device.

A conventional nonlinear optical device disclosed in U.S. Pat. No. 4,909,964 comprises means to direct at least one incident beam of electromagnetic radiation into an element. The element has nonlinear optical properties whereby electromagnetic radiation emerging from the element contains at least one frequency different from the frequency of any incident beam of radiation. The different frequency is an even multiple of the frequency of one incident beam of electromagnetic radiation.

Preferably, the emerging radiation of a different frequency is doubled (second-order) (SHG). Preferably, the electromagnetic radiation is radiation from one of a number of common lasers, such as Nd-YAG, Raman-shifted Nd-YAG, Nd-YLF or Nd-glass, semiconductor diode, Er-Glass, Ti-Sapphire, dye, and Ar or Kr ion, or radiation shifted to other frequencies by nonlinear processes. For example, polarized light of wavelength 1.06μ from an Nd-YAG laser is incident on the optical element along the optical path. A lens focuses the light into the optical element. Light emerging from the optical element is collimated by a similar lens and passed through a filter adapted to remove light of wavelength 1.06μ while passing light of wavelength 0.53μ.

As disclosed in U.S. Pat. No. 4,909,964 (incorporated herein by reference), one conventional electro-optic modulator comprises means to direct a coherent beam into an optical element, and means to apply an electric field to the element in a direction to modify the transmission property of the beam. For example, in an electro-optic modulator comprising an optical element, a pair of electrodes is attached to the upper and lower surfaces of the element, across which a modulating electric field is applied from a conventional voltage source. The optical element is placed between two polarizers. A light beam (such as that from a Nd-YAG laser) is polarized by a polarizer, focused on the optical element and propagated therethrough, and subjected to modulation by the electric field. The modulated light beam is led out through an analyzer polarizer. Linearly polarized light traversing the optical element is rendered elliptically polarized by action of the applied modulating voltage. The analyzer polarizer renders the polarization linear again. Application of the modulating voltage alters the birefringence of the optical element and consequently the ellipticity impressed on the beam. The analyzer polarizer then passes a greater or lesser fraction of the light beam as more or less of the elliptically polarized light projects onto its nonblocking polarization direction.

It will be further apparent to those skilled in the art that the optical elements formed by the crosslinked poled polymers of the present invention are useful in this and other devices utilizing their nonlinear properties, such as devices utilizing the electro-optic effect.

The present invention also concerns selected novel compounds that contain dye moieties and two or more reactive groups. Thus, this invention concerns a compound of the formula:

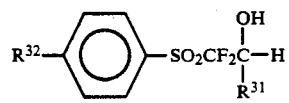

wherein:
$R^{31}$ is hydrocarbyl or heterocyclic group containing 3 to 6 carbon atoms;
$R^{32}$ is $-OR^{33}$, $-NHR^{34}$, or $R^{35}$;
$R^{33}$ is hydroxy substituted hydrocarbyl containing 1 to 20 carbon atoms;
$R^{34}$ is hydrocarbyl containing 1 to 20 carbon atoms, or hydroxysubstituted hydrocarbyl containing 1 to 20 carbon atoms; and
$R^{35}$ is a hydroxy substituted nonaromatic heterocyclic ring containing 3 to 6 carbon atoms and nitrogen in the heterocyclic ring, and said ring is attached to the phenyl group through said nitrogen atom.

In a preferred compound $R^{31}$ is phenyl, and $R^{32}$ is 2-hydroxymethyl-1-pyrrolidinyl.

This invention also concerns a compound of the formula:

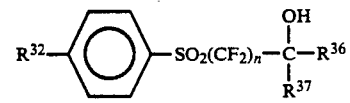

wherein:
$R^{32}$ is $-OR^{33}$, $-NHR^{34}$, or $R^{35}$;
$R^{33}$ is hydroxy substituted hydrocarbyl containing 1 to 20 carbon atoms;
$R^{34}$ is hydrocarbyl containing 1 to 20 carbon atoms, or hydroxysubstituted hydrocarbyl containing 1 to 20 carbon atoms;
$R^{35}$ is a hydroxy substituted nonaromatic heterocyclic ring containing 3 to 6 carbon atoms and nitrogen in the heterocyclic ring, and said ring is attached to the phenyl group through said nitrogen atom;
$R^{36}$ and $R^{37}$ are each independently hydrocarbyl containing 1 to 20 carbon atoms; and n is an integer of 2 to 10.

In a preferred compound n is 4. In a more preferred compound n is 4, $R^{32}$ is 2-hydromethyl-1-pyrrolidinyl, and $R^{36}$ and $R^{37}$ are both methyl.

This invention also provides a compound of the formula:

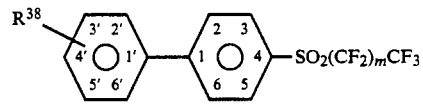

wherein:
m is zero or an integer from 1 to 9;
$R^{38}$ is $-NR^{39}(CH_2CR^{40}R^{41}OH)$ or $-N(CH_2CR^{40}R^{42}OH)_2$;
$R^{39}$ is hydrogen, hydrocarbyl Containing 1 to 20 carbon atoms or hydroxy substituted hydrocarbyl containing 1 to 20 carbon atoms;
$R^{40}$ is hydrogen or hydrocarbyl containing 1 to 20 carbon atoms; and
$R^{41}$ is hydroxymethyl, hydrogen or hydrocarbyl containing 1 to 20 carbon atoms;
$R^{42}$ is hydrogen or hydrocarbyl containing 1 to 20 carbon atoms; and
provided that $R^{38}$ is bound to the 3', 4', or 5' position of the biphenyl system, and at least one of $R^{39}$ and $R^{41}$ contains a hydroxyl group.

It is preferred if $R^{38}$ is bonded to the 4' position of the biphenyl system. It is also preferred if m is 2. In a preferred compound m is 2, $R^{38}$ is $-NHCH_2CH(OH)CH_2OH$, and $R^{38}$ is bonded to the 4' position of the biphenyl system. In another preferred compound, m is 2, $R^{38}$ is $-N[CH_2CH(OH)CH_3]_2$, and $R^{38}$ is bonded to the 4' position of the biphenyl system.

The syntheses of all of the above novel compounds are illustrated by the Examples. Homologs, as represented by the generic formulas, may be made by analogous methods, using similar chemical reactions, and homologous starting materials.

These novel compounds are useful as crosslinking agents for making crosslinked poled polymers useful in nonlinear optic applications.

In the Examples and Experiments, the following abbreviations are used:

| | |
|---|---|
| ACl | acryloyl chloride |
| DMAC | N,N-dimethylacetamide |
| EtOAc | ethyl acetate |
| EtOH | ethanol |
| GLMA | glycidyl methacrylate |
| ICEM | 2-isocyanatoethyl methacrylate |
| ICS | 4-isocyanatostyrene |
| MMA | methyl methacrylate |
| mR | molar ratio |
| Mw | peak average molecular weight |
| NLO | nonlinear optical |
| SHG | second harmonic generation |
| THF | tetrahydrofuran |

In the Examples, the poling apparatus consists of a sample holder constructed so that the sample normal is to the beam direction. The laser beam is polarized so that the electric vector is in the plane defined by the sample normal and the beam. Heaters are incorporated into the sample holder so that the temperature of the sample can be maintained anywhere in the temperature range from room temperature to 200° C. A standard corona charging unit from a xerographic copy machine is positioned over the sample to apply an electric field. Appropriate holes are cut in the sample holder and the corona charging unit to allow both the fundamental beam and any second harmonic light to pass through the sample and be detected.

In some of the following Examples, certain crosslinking agents are used. Their designations are given below (some of the crosslinking agents are designated in certain Examples and Experiments).

Crosslinking Agent H: 1,4-nitrophenylglycerol

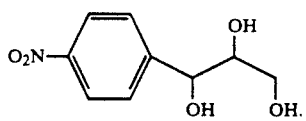

The compound was obtained commercially from FluKa Chemical Company, Inc. (Stock #73678)

Crosslinking Agent J: p-nitrophenyl-alpha-L-arabinofuranoside,

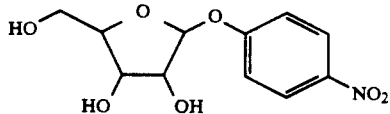

The compound was obtained commercially from Sigma Chemical Company, Inc. (Stock #N1381)

Crosslinking Agent K: 4-nitrocatechol

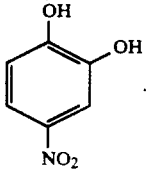

The compound was obtained commercially from Aldrich Chemical Company, Inc. (Stock #N15553)

Crosslinking Agent L: 2-amino-5-nitrophenol

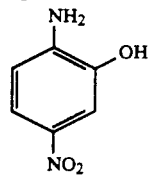

The compound was obtained commercially from Aldrich Chemical Company, Inc. (Stock #A70607)

Crosslinking Agent M: 4-nitro-1,2-phenylenediamine

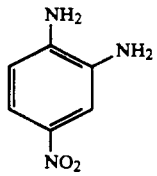

The compound was obtained commercially from Aldrich Chemical Company, Inc. (Stock #108898)

Crosslinking Agent N: Disperse Red 19

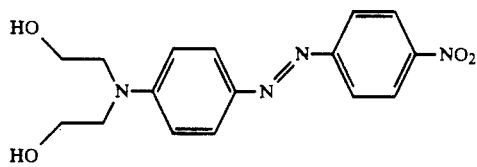

The compound was obtained commercially from Sigma Chemical Company, Inc. (Stock #D-1642). It was purified by soxhlet extraction using methylene chloride and recrystallization.

EXPERIMENT 1

Reactive Polymers

Procedure A: Preparation of Copolymers of Acryloyl Chloride, Isocyanatoethyl Methacrylate and Glycidyl Methacrylate with Methyl Methacrylate Into a set of 30 ml vacuum dried serum bottles were placed 0.05 g Vazo-52 (α,α'-azobis(α,γ-dimethylvaleronitrile)) initiator, the appropriate amount of freshly distilled sodium dried THF (tetrahydrofuran) and mixtures of freshly purified monomers as designated in Table 1-A-1. The bottles were flushed with dry nitrogen, sealed and placed in an ultrasonic bath at 50° C. for 48 hours. After removal from the bath the samples were stored in the sealed bottles until ready for use. Samples were removed by syringe under positive nitrogen pressure and introduced into an NLO active crosslinking agent solution just before spin-coating onto conductive substrates as described in the Examples. Bottles were resealed under dry nitrogen to retain an anhydrous inert atmosphere. Acryloyl chloride, isocyanatoethyl methacrylate, and glycidyl methacrylate were purified by distillation. Methyl methacrylate was purified by passing through basic alumina.

TABLE I-A-1

| #  | Monomer | mR | Weight (g) | Volume (ml) | moles  | THF (ml) | Mw (Ave) |
|----|---------|----|------------|-------------|--------|----------|----------|
| A1 | MMA     | 19 | 6.682      | 7.078       | 0.0668 | 21       | 30,700   |
|    | ACl     | 1  | 0.318      | 0.286       | 0.0035 |          |          |
| A2 | MMA     | 9  | 6.360      | 6.737       | 0.0636 | 21       | 28,800   |
|    | ACl     | 1  | 0.639      | 0.574       | 0.0071 |          |          |
| A3 | MMA     | 4  | 5.708      | 6.047       | 0.0571 | 21       | 18,600   |
|    | ACl     | 1  | 1.291      | 1.159       | 0.0142 |          |          |
| A4 | MMA     | 2  | 4.819      | 5.105       | 0.0482 | 21       | —        |
|    | ACl     | 1  | 2.180      | 1.957       | 0.0241 |          |          |
| A5 | MMA     | 1  | 3.674      | 3.892       | 0.0367 | 21       | 26,400   |
|    | ACl     | 1  | 3.325      | 2.985       | 0.0367 |          |          |
| A6 | ACl     | 1  | 15.0       | 13.46       | 0.1657 | 15       | 3,800    |
| B1 | MMA     | 9  | 4.318      | 4.574       | 0.0432 | 20       | —        |
|    | GLMA    | 1  | 0.681      | 0.653       | 0.0048 |          |          |
| B2 | MMA     | 4  | 3.690      | 3.908       | 0.0369 | 20       | —        |
|    | GLMA    | 1  | 1.309      | 1.257       | 0.0092 |          |          |
| B3 | MMA     | 2  | 2.923      | 3.097       | 0.0292 | 20       | —        |
|    | GLMA    | 1  | 2.076      | 1.992       | 0.0146 |          |          |
| B4 | MMA     | 1  | 2.066      | 2.188       | 0.0206 | 20       | —        |
|    | GLMA    | 1  | 2.933      | 2.815       | 0.0206 |          |          |
| B5 | GLMA    | 1  | 5.0        | 4.798       | 0.0352 | 20       | —        |
| C1 | MMA     | 9  | 2.559      | 2.711       | 0.0256 | 27       | 23,000   |
|    | ICEM    | 1  | 0.440      | 0.4262      | 0.0028 |          |          |
| C2 | MMA     | 4  | 2.162      | 2.290       | 0.0216 | 27       | 25,300   |
|    | ICEM    | 1  | 0.837      | 0.810       | 0.0054 |          |          |
| C3 | MMA     | 2  | 1.690      | 1.790       | 0.0169 | 27       | 25,300   |
|    | ICEM    | 1  | 1.309      | 1.266       | 0.0084 |          |          |
| C4 | MMA     | 1  | 1.176      | 1.246       | 0.0118 | 27       | 18,900   |
|    | ICEM    | 1  | 1.823      | 1.763       | 0.0118 |          |          |
| C5 | ICEM    | 1  | 3.0        | 2.901       | 0.0193 | 27       | 4,900    |

Procedure B: Preparation of Homopolymers of Glycidyl Acrylate, Glycidyl Methacrylate, and Isocyanatoethyl methacrylate Into 100 ml round bottom flasks containing magnetic stirrers and fitted with reflux condensers, thermometers and nitrogen bubblers were placed 0.05 g Vazo-64 (α,α'-azobis(isobutyronitrile)) initiator and 40 ml freshly distilled sodium dried THF with 10 ml of either glycidyl acrylate or glycidyl methacrylate or 45 ml THF and 5 ml isocyanatoethyl methacrylate. The rapidly stirred solutions were then heated to 55° C. for 48 hours using an oil bath for maintaining uniform temperature control. The polymeric product mixtures were transferred to 60 ml serum bottles, flushed with nitrogen, sealed and stored until ready for use. Samples were removed by syringe under positive nitrogen pressure and introduced into an NLO active crosslinking agent solution just before spincoating onto conductive substrates as described in the Examples. Bottles were resealed under nitrogen to retain an anhydrous inert atmosphere.

Procedure C: Preparation of Polyisocyanatostyrene and Styrene-Isocyanatostyrene (S-ICS) Copolymers Step 1

Into a three necked round bottom flask fitted with a reflux condenser, bubblers to monitor passage of nitrogen and reagent gasses, a mechanical stirrer, and a gas addition tube were placed toluene that had been dried over molecular sieves, styrene, and p-aminostyrene in amounts described in Table I-C-1. Hydrogen chloride gas was then passed into the mixture while stirring until the mixture became saturated, as evidenced by comparing the rate of gas evolution from the reactor to the input rate. Off-gas was trapped using concentrated sodium hydroxide. The reaction temperature was increased during HCl addition to 90° C. and a solid dispersion of p-aminostyrene hydrochloride was formed. Time to reach saturation was about 20 minutes, however gas addition was continued for 1 hour. Temperature was maintained at 90° C. using a regulated oil bath.

Step 2

Upon completion of step 1, the input gas was shifted from HCl to phosgene. The reactive gas was passed into the reactor until conversion of aminostyrene hydrochloride to p-isocyanatostyrene was complete. This was evidenced by the disappearance of the insoluble p-aminostyrene hydrochloride salt, formation of a clear reaction medium and a balance between input and off-gas flow rates. The time for clearing was about 1 hour. Addition of phosgene was continued for 2 hours.

Step 3

When the reaction was complete, the product mixture was cooled to 70° C. and purged with nitrogen for 60 minutes to remove dissolved unreacted gasses. 0.1 Grams of Vazo-64 (a,a'-azobis(isobutyronitrile)) initiator was then added and polymerization allowed to proceed overnight before isolation of the reactive polymer reagent product.

Step 4

The polymer reagent was precipitated in dry hexane, decanted, washed with additional hexane, decanted and then dissolving in dry THF. The resultant mixture was finally centrifuged to remove residual insoluble salts and impurities then transferred to nitrogen flushed serum bottles for storage. Analytical data is given in Table I-C-1.

TABLE I-C-1

Reagents, Reaction Parameters and Analysis Data for Styrene-Isocyanatostyrene Polymers

| Sample # | 1 | 2 | 3 |
|---|---|---|---|
| Composition (S-ICS) (Theory) | 0–1 | 0.87–1 | 1.75–1 |
| Styrene (g) | 0.0 | 10.0 | 20.0 |
| [moles] | [0.0] | [0.096] | [0.192] |
| P-Aminostyrene (g) | 10.0 | 10.0 | 10.0 |

TABLE I-C-1-continued

Reagents, Reaction Parameters and Analysis Data for Styrene-Isocyanatostyrene Polymers

| Sample # | 1 | 2 | 3 |
|---|---|---|---|
| [moles] | [0.084] | [0.084] | [0.084] |
| Toluene (ml) | 100 | 100 | 200 |
| Mw (average) | 3550 | 16450 | 11550 |
| Elemental Anal. (T/A) | | | |
| Carbon | 74.47/74.02 | 81.93/81.24 | 84.95/83.50 |
| Hydrogen | 4.86/5.01 | 6.06/6.29 | 6.56/6.51 |
| Nitrogen | 9.65/8.92 | 5.62/4.78 | 3.96/4.01 |
| Composition (S-ICS) (Actual by C, H, N) | 0–1 | 1.12–1 | 1.69–1 |

EXAMPLE 1

Preparation of Crosslinking Agent A

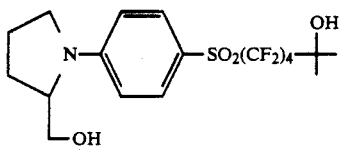

Step 1

To 1.00 g (6.66 mmoles) sodium 4-fluorothiophenoxide, in 10 ml of dimethyl formamide was added to 3.023 g (6.66 mmoles) of 1,4-diiodoperfluorobutane at −50° C. The mixture was kept at −50° C. for one hour and then stirred at room temperature for three days. The solvent was removed and the residue was chromatographed on silica gel with hexane to give 0.736 g ( 1.6 mmoles, 24%) of 4-fluorophenyl-S(CF2)4I. $^1$H nmr (CD$_2$Cl$_2$): 7.7 (m, 2H) and 7.15 (m, 2H). 19F nmr (CD2Cl2): −109 (m, 1F), −112.5 (m, 2F), −118.4 (m, 2F), −87.5 (m, 2F), −59.3 (m, 2F).

Step 2

To 0.026 g (0.45 mmoles) of acetone in 5 ml of ether was added 0.100g (0.220 mmoles) of 4-fluorophenyl-S(CF$_2$)$_4$I. The mixture was cooled to −100° C. (hexane/liquid nitrogen slush) and 0.15 ml (1.6 M, 0.242 mmoles) of n-butyl Lithium was added. The mixture was warmed to room temperature, saturated ammonium chloride solution was added and the mixture extracted with ether. The organic layer was dried over MgSO$_4$. The solvent was removed by rotary evaporation and the residue chromatographed on silica gel with 50% CHCl$_3$/hexane to give 22 mg (0.057 mmoles, 25%) of the desired product, 4-fluorophenyl-S(CF$_2$)$_4$C(CH$_3$)$_2$OH, as a colorless liquid. $^1$H nmr (CD$_2$Cl$_2$): 7.7 (m, 2H), 7.15 (m, 2H), 2.2 (s, 1H), 1.4 (m, 6H). $^{19}$F nmr (CD$_2$Cl$_2$): −87.2 (m,2F), −109.4 (m, 1F), −118.6 (m, 2F), −119.4 (m, 2F), −121.8 (m, 2F).

Step 3

To 2.76 g (7.15 mmoles) of 4-fluorophenylS(CF$_2$)$_4$C(CH$_3$)$_2$OH in 25 ml of glacial acetic acid was added 2.858 g (28.5 mmoles) of CrO$_3$. The mixture was refluxed for two days. The reaction mixture was then added to 100 ml of ice water and extracted with 3×75 ml ether. The ether extract was washed with 3×50 ml water, dried over MgSO$_4$ and the solvent evaporated. The residue was chromatographed on silica gel diluted with 25% EtOAc/hexane to give 2.528 g (6.0 mmoles, 84%) of 4-fluorophenyl-SO$_2$(CF$_2$)$_4$C(CH$_3$)$_2$OH. $^1$H nmr (CD$_2$Cl$_2$): 8.1 (m, 2H), 7.4 (m, 2H), 2.1 (s, 1H), 1.4 (m, 6H).

Step 4

To 0.315 (0.753 mmoles) of 4-fluorophenyl-SO$_2$(CF$_2$)$_4$C(CH$_3$)$_2$OH and 0.076 g (0.753 mmoles) of (S)-(+)-2-pyrrolidinemethanol in 2 ml of dimethyl sulfoxide was added 0.110 g (0.796 mmoles) of K$_2$CO$_3$. The mixture was heated at 50° C. overnight. About 10 ml of water was added to form a paste which was collected on a spatula and washed with water. The white paste was vacuum dried to give 0.313 g (0.63 mmoles , 83%) of the desired crosslinking agent. $^1$H nmr (CD$_2$Cl$_2$): 7.65 (d, 2H), 6.8 (d, 2H),4.0 (m, 1H), 3.7(m, 1H), 3.6 (m, 1H), 3.5 (m, 1H), 3.3(m, 1H), 2.6 (s, 1H), 2.2 (s, 1H), 2.1 (m, 3H), 1.7 (m, 1H), 1.4 (m, 6H).

EXAMPLE 2

Preparation of Crosslinking Agent B

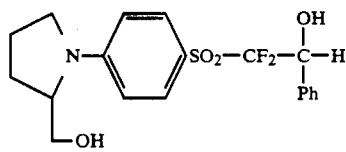

Step 1

In accordance with the procedure described in G. Patrick Stahly, U.S. Pat. No. 4,837,327, 10.00 g (0.250 moles ) of NaOH was dissolved in 13 ml of water and added to 15 ml of p-dioxane in a Fischer-Porter bottle. 5.75 ml (0.054 moles) of 4-fluorothiophenol was added. A white solid formed. 10 ml of water was added to facilitate stirring and the Fischer-Porter bottle was pressurized with 52 psi of CHF$_2$Cl and heated to 70° C. The bottle was periodically repressurized to 50 psi with CHF$_2$Cl over a period of 1 hour. The reaction mixture was cooled to room temperature and 50 ml of water added. The mixture was extracted with 3×15 ml ether. The solvent was removed from the organic layer, the residue dissolved in 50 ml of pentane and washed with 5×10 ml of water. After drying over MgSO$_4$, the pentane was removed and the residue distilled to give 0.57 g (3.2 mmoles, 5.9%) of the product, 4-fluorophenyl-SCF$_2$H, which was collected at 56°-57° C. (10 mm) as a colorless liquid. $^1$H nmr (CD$_2$Cl$_2$): 7.6 (m, 2H), 7.1 (m, 2H), 6.8 (t, 1H). $^{19}$F nmr (CD$_2$Cl$_2$): −92.5 (d, J=56.8Hz).

Step 2

To 2.10 g (0.0118 moles) of 4-fluorophenyl-SCF$_2$H in 50 ml of CH$_2$Cl$_2$ was added 9.24 g (55%, 0.029 moles) of MCPBA (3-chloroperoxybenzoic acid) in 120 ml of CH$_2$Cl$_2$ dropwise. The mixture was stirred at room temperature overnight. Saturated NaHCO$_3$ (100 ml) was added and the mixture was extracted with 3×100 ml CH$_2$Cl$_2$. The organic layer was washed with 150 ml of water and then dried over MgSO$_4$. The solvent was removed and the residue chromatographed on silica gel diluted with CHCl$_3$. Following drydown, 2.008g (0.0095 moles, 81%) of the desired product, 4-fluorophenyl-SO$_2$CF$_2$H was obtained as a white solid. $^1$H nmr (CD$_2$Cl$_2$): 8.1 (m, 2H), 7.4 (m, 2H), 6.2 (t, 1H). $^{19}$F nmr (CD$_2$Cl$_2$): −100.2 (m, 1F), −122.14 (d, J=53.3 Hz, 2F).

Step 3

To a mixture containing 1.00 g (4.76 mmoles) of 4-fluorophenyl-SO$_2$CF$_2$H in 7 ml of CH$_2$Cl$_2$ and 9 ml of 50% NaOH in water was added 2 drops of Aliquat 336 (tricaprylymethylammonium chloride; a mixture of C$_8$ and C$_{10}$ chains with C$_8$ predominating. Registered trademark of Henkel Corporation) and 1.555 g (14.7 mmoles) of benzaldehyde. After stirring for 1.5 hrs, about 1.5 ml additional CH$_2$C$_{12}$ was added to help stirring. The mixture was stirred further for an additional 2 hrs. The mixture was added to 100 ml of 1N HCl and extracted with 2×75 ml of CH$_2$Cl$_2$. After drying the organic layer over MgSO$_4$ and stripping off the solvent, the residue was chromatographed over silica gel diluted with CH$_2$Cl$_2$. The material collected was washed with hexane and the resulting white solid vacuum dried to give 0.694 g (2.28 mmoles, 47.9%) of the desired product, 4-fluorophenyl-SO$_2$CF$_2$-C(Ph)(H)(OH). $^1$H nmr (CD$_2$Cl$_2$): 8.0 (m, 2H), 7.4 (m, 5H), 7.3 (m, 2H), 5.6 (d, 1H), 3.2 (s, 1H).

Step 4

To 0.213 (0.676 mmole) of 4-fluorophenyl-SO$_2$CF$_2$C(Ph)(H)(OH) and 0.068 g (0.676 mmoles) of (S)-(+)-2-pyrrolidinemethanol in 5 ml of dimethyl sulfoxide was added 0.100 g (0.723 mmoles) of K$_2$CO$_3$. The mixture was heated at 60° C. overnight. About 10 ml of water was added to precipitate the crosslinking agent as a yellow paste which forms a yellow oil on standing, 0.156 g (0.39 mmoles, 58%).

EXAMPLE 3

Preparation of Crosslinking Agent C

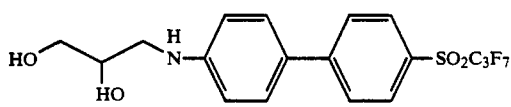

Step 1: Preparation of 4-bromophenyl-SO$_2$C$_3$F$_7$

The sodium salt of 4-bromobenzenethiol was reacted with perfluoropropyl iodide to give an intermediate phenyl prefluoropropyl sulfide which was oxidized to the sulfone using chromium trioxide (see, N. V. Kondratenko, V. I. Popov, A. A. Kolomeitsev, E. P. Saenko, V. V. Prezhdo, A. E. Lutskii and L. M. Yagupolskii, J. Org. Chem. USSR (Engl. Trans.) 1980, 16, 1049). For references on the use of the analogous sodium salt of 4-fluorobenzenethiol: V. N. Boiko, G. M. Shchupak and L. M. Yagupolskii, J. Org. Chem. USSR (Engl. Trans.) 1977, 13, 972; V. I. Popov, V. N. Boiko and L. M. Yagupolskii, J. Org. Chem. USSR (Engl. Trans.) 1977, 13, 1985; V. N. Boiko, T. A. Dashevskaya, G. M. Shchupak and L. M. Yagupolskii, J.Org. Chem. USSR (Engl. Trans.) 1979, 15, 347).

To 10.0 g (47.4 mmoles) of the sodium salt of 4-bromobenzenethiol in 90 ml of DMF at 0° C. was added 14.10 g (47.6 mmoles) of n-perfluoropropyl idodide. After stirring at room temperature overnight, the mixture was poured into 200 ml of ice water, extracted with 3×100 ml of CH$_2$Cl$_2$ and dried over Na$_2$SO$_4$. After filtering, the solution was concentrated on a rotary evaporator and the residue distilled to give 6.12 g of 4-bromophenylperfluoropropyl sulfide (46° C./0.19 mm). To 5.91 g (0.165 moles) of this sulfide in 50 ml of glacial acetic acid was added 6.60 g (0.066 moles) of CrO$_3$. The mixture was refluxed overnight. The cooled mixture was then poured into 150 ml of ice water and extracted with 3×150 ml of ether. The ether extract was washed with 100 ml of water and dried over Na$_2$SO$_4$. The solvent was removed and the solid residue washed with water to give 5.091 g (0.013 moles, 79%) of 4-bromophenylperfluoropropyl sulfone. Elemental analysis calculated for C$_9$H$_4$F$_7$BrSO$_2$: C: 27.78; H: 1.04; Found: C: 27.61; H: 0.98. Mp: 63°-65° C. $^1$H nmr (CD$_2$Cl$_2$): 7.9 (m).

Step 2: Preparation of

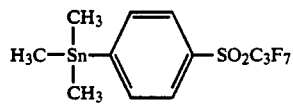

2.001g (5.14 mmoles) of 4-bromophenyl-SO$_2$C$_3$F$_7$ and 200 mg of Pd(PPh$_3$)$_4$ were stirred for 10 minutes in about 35 ml of toluene. To this mixture was added 3.370 g (10.3 mmoles) of Me$_3$SnSnMe$_3$ in 10 ml of toluene. The mixture was refluxed overnight. Solvent was removed by rotary evaporation and the reside was vacuum distilled to give 1.26 g (2.7 mmoles, 52.5%) of the desired product, a colorless liquid (bp=127°-131° C.@25 mm), which solidified upon standing at room temperature. Elemental analysis calculated for Cl$_2$H$_{13}$O$_2$F$_7$SSn: C: 30.47; H: 2.77; Found: C: 30.88; H: 2.38. $^1$H nmr (CD$_2$Cl$_2$): 7.9(d, 2H), 7.8 (d, 2H), 0.4 (s with Sn satellite, 9H).

Step 3: Preparation of

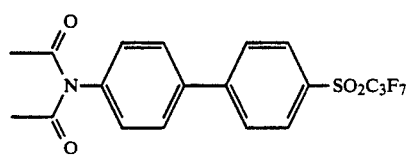

Two and a half g (9.75 mmoles) of 4-bromo-phenylN[CH$_3$C(O)]$_2$ and 200 mg of Pd(PPh3)$_4$ were stirred for 15 minutes in about 20 ml of dioxane. To this mixture was added 4.61 g (9.75 mmoles) of 4-trimethylstannylphenylSO$_2$C$_3$F$_7$ in 35 ml of dioxane. The mixture was refluxed for two days. Solvent was removed and the residue chromatographed with 25% EtOAc/hexane to give 2.622 g (5.4 mmoles, 55%) of the desired product as a white solid. Elemental analysis calculated for C$_{19}$H$_{14}$NO$_4$F$_7$S: C: 47.02; H: 2.91; Found: C: 46.77; H: 3.05. $^1$H nmr (CD$_2$Cl$_2$): 8.1 (d, 2H), 7.9 (d, 2H), 7.7 (d, 2H), 7.3 (d, 2H), 2.3 (s, 6H)).

Step 4: Preparation of

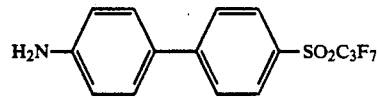

The product from step 3 (2.602 g,5.36 mmoles) was added 10 ml of EtOH and 10 ml of concentrated HCl was added. The mixture was refluxed for two hours. To the cooled solution was added 2N NaOH to pH of 7 and the solid filtered and washed with water. Thus obtained was 2.093 g of the desired product (5.21 mmoles, 97%).

Elemental analysis calculated for $C_{15}H_{10}NO_2F_7S$: C: 44.90; H: 2.51; Found: C 44.02; H: 2.48. $^1H$ nmr $(CD_2Cl_2)$: 8.0 (d, 2H), 7.8 (d, 2H), 7.5 (d, 2H), 6.8 (d, 2H), 4.0 (s, 2H).

Step 5: Preparation of

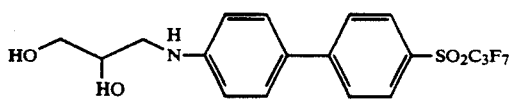

To 1.00g (2.49 mmoles) of 4'-aminobiphenylyl-$SO_2C_3F_7$ in 40 ml of EtOH was added 0.330 g (2.55 mmoles) of 2,3-epoxypropyl acrylate. The mixture was refluxed overnight. The solvent was removed and the residue flash chromatographed on silica gel eluted with 50% EtOAc/hexane to give 0.672 g of the starting biphenyl and 0.32 g of the desired product. Elemental analysis calculated for $C_{18}H_{16}F_7SO_4N$: C: 45.48; H: 3.39; Found: C: 45.43; C: 3.57. $^1H$ nmr (THF-$d_8$): 8.0 (d, 2H), 7.9 (d, 2H), 7.6 (d, 2H), 6.7 (d, 2H), 5.4 (m, 1H), 4.1 (d, 1H), 3.8 (t, 1H), 3.7 (m, 1H), 3.5 (d of t, 2H), 3.3 (m, 1H), 3.1 (m, 1H).

EXAMPLE 4

Preparation of Crosslinking Agent D

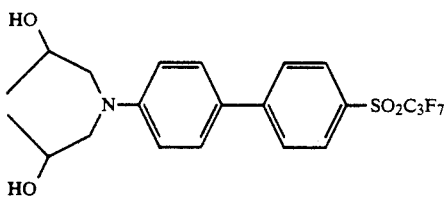

In 5 ml of ethanol was added 0.200 g (0.498 mmoles) of 4-aminobiphenylyl-$SO_2C_3F_7$ and 0.70 ml (9.97 mmoles) of propylene oxide. The mixture was heated at 80° C. in a Fischer-Porter bottle for six days. Solvent was removed and the residue chromatographed on silica gel eluted with 50% EtOAc/hexane to give 0.142 g of the desired product (0.27 mmoles, 55%) as a light yellow solid. Elemental analysis calculated for $C_2H_{22}NO_4F_7S$: C: 48.74; H: 4.29; Found: C: 48.49; H: 4.22. $^1H$ nmr $(CD_2Cl_2)$: d at 8.0, 7.8, 7.6, 7.55, 6.9, 6.7, 4.2 (m), d of d at 3.7, 3.5, 3.3, 3.1, 1.6 (broad s), d at 1.25 and 1.2.

EXPERIMENT 2

Preparation of Crosslinking Agent E

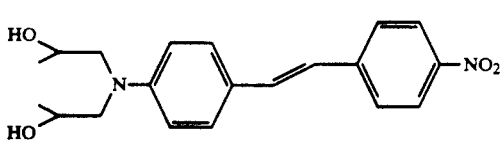

To 0.400 g (1.66 mmoles) of 4-nitro-4'-aminostilbene (J. Chem. Soc., 1942, p 112 and J. Chem. Soc. Chem. Commt., CC 1987, p 1424) in 10 ml of EtOH was added 2.33 ml (33.3 mmoles) of propylene oxide. The mixture was heated at 80° C. for 5 days. The mixture was cooled and filtered. The product was washed with EtOH to give 0.367 g (1.0 mmoles, 62%) of the desired product. $^1H$ nmr $(CD_2Cl_2)$: d at 8.2, 7.6, 7.5, 6.8, 6.6, olefinic protons at 7.2 (d), 7.0 (d), 4.2 (m), d of d at 3.7, 3.5, 3.3 and 3.1, HO- resonances at 3.5 and 2.6.

EXPERIMENT 3

Crosslinking Agent F

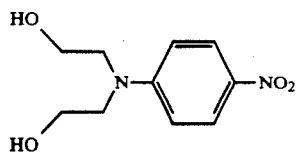

A mixture containing 5.00 g (0.0354 moles) of the 4-fluoro-nitrobenzene, 5.583g (0.0531 moles) of diethanolamine and 4.95 g (0.0358 mmoles) of $K_2CO_3$ in 25 ml of DMF was heated at 100° C. overnight. 50 ml of water was added to the cooled mixture and then it was extracted with $5 \times 100$ ml of $CH_2Cl_2$. The organic layer was dried over $Na_2SO_4$. Hexane was added to precipitate the product. The product was filtered and washed with hexane to give 5.776 g of orange-yellow solid. (0.025 moles, 72%). $^1H$ nmr $(CD_2Cl_2)$: 8.1 (m, 2H), 6.7 (m, 2H), 3.9 (t, 4H), 3.7 (t, 4H), 2.8 (s, 2H).

Note: A literature reference for preparation of a similar compound, $(HOCH_2CH_2)_2$-phenyl-CHO is: R. N. DeMartino, U.S. Pat. No. 4,757,130, Jul. 12, 1988.

EXPERIMENT 4

Crosslinking Agent G

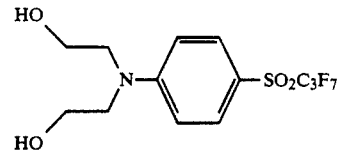

Step 1: Preparation of 4-Fluorophenylperfluoropropyl sulfone

To 10.0 g (66.6 mmoles) of the sodium salt of 4-flurobenzenethiol in 100 ml of DMAC at 0° C. was added 19.71 g (66.6 mmoles) of 1-iodoperfluoropropane. After stirring at room temperature overnight, the mixture was poured into 75 ml of saturated $NH_4Cl$ solution, and extracted with $3 \times 75$ ml of ether. The ether extract was washed with 50 of water and dried over $MgSO_4$. After filtering, the solution was concentrated on a rotary evaporator and the residue distilled to give 15.77 g of 4-fluorophenylperfluoropropyl sulfide (56° C./10 mm). To 7.573 g (0.0256 moles) of this sulfide in 75 ml of glacial acetic acid was added 10.227 g (0.102 moles) of $CrO_3$. The mixture was refluxed overnight. The cooled mixture was then poured into 150 ml of ice water and extracted with $3 \times 100$ ml of ether. The ether extract was dried over $MgSO_4$. The solvent was removed and the residue was Kugelrohr distilled at 0.1 mm at 35°-50° C. to give 6.40 g (0.0195 mmoles, 76.2%) of 4-fluorophenyl perfluoropropyl sulfone as a colorless liquid. 1H nmr $(CD_2Cl_2)$: 8.1 (m, 2H), 7.4 (m, 2H).

Step 2: Preparation of $(HOCH_2CH_2N)_2$-p-phenylene-$SO_2C_3F_7$

To 0.508 g (1.55 mmoles) of the above sulfone in 1 ml of DMF was added 0.163 g (1.55 mmoles) of diethanolamine in 1 ml of DMF and 0.220 g (1.59 mmoles) of K₂CO₃ slurry in 1 ml of DMF. The mixture was heated at 100° C. overnight. To the cooled mixture was added ml of water and extracted with 3×35 ml of ether. The ether extract was dried over Na₂SO₄. Solvent was removed and the residue was chromatographed on silica gel with 50% EtOAc/hexane and then eluted with EtOAc. Thus obtained was 0.292 g (0.707 mmoles, 46%) of the desired product as a white solid. ¹H nmr (CD₂Cl₂): 7.8 (m, 2H), 6.9 (m, 2H), 3.9 (t, J=5 Hz, 4H), 3.7 (t, J=Hz, 4H), 2.8 (s, 2H).

EXAMPLE 5

Polyisocyanatoethylmethacrylate -

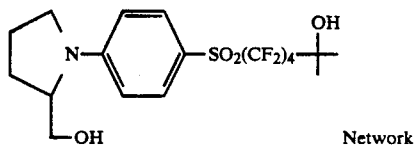

Network

A 10% by weight solution of polyisocyanatoethylmethacrylate prepared by procedure I-A (sample C5) was prepared in tetrahydrofuran. To 0.3 ml of this solution was added 0.0461 g (0.0923 mmole) of crosslinking agent A in 0.2 ml of tetrahydrofuran. An additional 0.3 ml of tetrahydrofuran was added. The resulting solution was spin coated onto a glass slide coated with indium tin oxide. The resulting film was dried 20 hours under nitrogen. The sample was placed in the poling apparatus so that it could be poled while monitoring the second harmonic signal which was generated. An electric field was applied and an SHG signal equal to about 80% of the maximum observed during the course of the poling process was observed within 10 min. The sample was then heated to 50° C. at a heating rate of approximately 1.0° C./min. The film was maintained at 50° C. for =90 min. to partially crosslink the film. The sample was then heated to 80° C. at a rate of 0.4° C./min. The sample was then rapidly cooled to room temperature at which time the electric field was removed. When the field was removed the SHG signal decreased by a factor of three over a period of one day. After one day the SHG signal was very stable, decreasing at a rate of about 0.6%/day.

EXAMPLE 6

Polyisocyanatoethylmethacrylate -

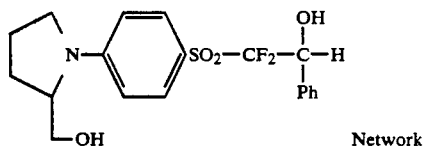

Network

The procedure of Example 5 for preparing a film sample for poling was followed except that 0.0316 g (0.076 mmole) of crosslinking agent B was used instead of crosslinking agent A. The resulting solution was spin coated onto a glass slide coated with indium tin oxide. The resulting film was dried 22 hours under nitrogen. The sample was placed in the poling apparatus so that it could be poled while monitoring the second harmonic signal which was generated. An electric field was applied and an SHG signal equal to about 100% of the maximum observed during the course of the poling process was observed within 10 min. The sample was then heated to 60° C. at a heating rate of approximately 1.0° C./min. The film was maintained at 60° C. for 10 min. to partially crosslink the film. The sample was then heated to 80° C. at a rate of 1.0° C./min. The sample was held at 80° C. for 10 min. to further crosslink the film. The sample was then heated at a rate of 1.0° C./min to 100° C. At this time the field was turned off and the SHG signal observed to fall to about 10% Of its Original value in a period of 2 min. The field was reapplied and the SHG signal restored to nearly the value it had before removal of the field. The sample was then heated at a rate of 1.0° C./min to 120° C. for further curing. It was then rapidly cooled back to 100° C. and the field removed to determine if additional stability had occurred by heating to 120° C. The SHG signal was observed to fall by only 10% in a period similar to that which had resulted in a 90% decrease before the additional heating, indicating that additional crosslinking had taken place. The sample was then rapidly cooled to room temperature at which time the electric field was removed. When the field was removed the SHG signal decreased approximately 15% over a period of one day. After one day the SHG signal was very stable decreasing at a rate of about 0.4%/day.

EXAMPLE 7

Isocyanatoethylmethacrylate-methyl methacrylate (1-1 copolymer)

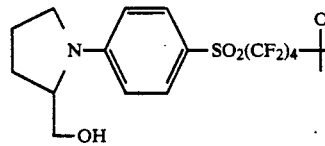

Network

A 10% by weight solution of polyisocyanatoethylmethacrylate prepared by procedure I-A (sample C4) was prepared in tetrahydrofuran. To 0.4 ml of this solution was added 0.0206 g (0.052 mmole) of crosslinking agent B in 0.2 ml of tetrahydrofuran. An additional 0.3 ml of tetrahydrofuran was added. The resulting solution was spin coated onto a glass slide coated with indium tin oxide. The resulting film was dried 39 hours under nitrogen. The sample was placed in the poling apparatus so that it could be poled while monitoring the second harmonic signal which was generated. An electric field was applied and an SHG signal equal to about 50% of the maximum observed during the course of the poling process was observed within 10 min. The sample was then heated to 60° C. at a heating rate of approximately 1.7° C./min. The film was maintained at 60° C. for 10 min. to partially crosslink the film. The sample was then heated to 80° C. at a rate of ≈1.5° C./min. The sample was then rapidly cooled to room temperature at which time the electric field was removed. When the field was removed the SHG signal decreased by ≈30% over a period of one day. After one day the SHG signal was very stable, decreasing at a rate of about 0.5%/day.

EXAMPLE 8

Isocyanatoethylmethacrylate-methyl methacrylate (1-4 Copolymer) -

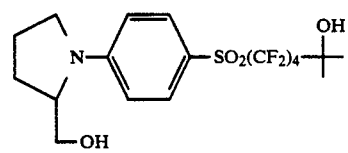

Network

A 10% by weight solution of polyisocyanatoethylmethacrylate prepared by procedure I-A (sample C2) was prepared in tetrahydrofuran. To 0.6 ml of this solution was added 0.0212 g (0.0534 mmole) of crosslinking agent B in 0.2 ml of tetrahydrofuran. An additional 0.3 ml of tetrahydrofuran was added. The resulting solution was spin coated onto a glass slide coated with indium tin oxide. The resulting film was dried 47 hours under nitrogen. The sample was placed in the poling apparatus so that it could be poled while monitoring the second harmonic signal which was generated. An electric field was applied and an SHG signal equal to about 6% of the maximum observed during the course of the poling process was observed within 10 min. The sample was then heated to 110° C. at a heating rate of approximately 0.7° C./min. This slow heating rate was use to partially crosslink the film while the temperature was being increased. The sample was then rapidly cooled to room temperature at which time the electric field was removed. When the field was removed the SHG signal decreased by $\approx$30% over a period of one day. After one day the SHG signal was very stable, decreasing at a rate of about 0.7%/day.

EXAMPLE 9

Isocyanatoethylmethacrylate-methyl methacrylate (1-9 copolymer) -

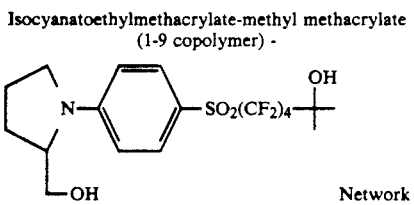

Network

A 10% by weight solution of polyisocyanatoethylmethacrylate prepared by procedure I-A (sample C1) was prepared in tetrahydrofuran. To 0.8 ml of this solution was added 0.0147 g (0.037 mmole) of crosslinking agent B in 0.2 ml of tetrahydrofuran. An additional 0.3 ml of tetrahydrofuran was added. The resulting solution was spin coated onto a glass slide coated with indium tin oxide. The resulting film was dried in vacuum at room temperature for 15 min. The sample was placed in the poling apparatus so that it could be poled while monitoring the second harmonic signal which was generated. An electric field was applied and an SHG signal equal to about 100% of the maximum observed during the course of the poling process was observed within 10 min. The sample was then heated to 60° C. at a heating rate of approximately 0.7° C./min. The film was maintained at 60° C. for 10 min. to partially crosslink the film. The sample was then heated to 90° C. at a rate of 0.9° C./min. The sample was then rapidly cooled to room temperature at which time the electric field was removed. When the field was removed the SHG signal decreased by a factor of three over a period of one day. After one day the SHG signal was very stable, decreasing at a rate of about 2.0%/day.

EXAMPLE 10

Polyisocyanatoethylmethacrylate - 4-nitro-1,2-phenylenediamine Network

The procedure of Example 5 for preparing crosslinked poled polymer was followed except that 0.01438 g (0.094 mmole) of crosslinking agent M (4-nitro-1,2-phenylene-diamine) in 0.2 ml of tetrahydrofuran was used instead of the solution of crosslinking agent prepared in Example 5. To this mixture was added 0.2 ml of the 10% by weight solution of polyisocyanato-ethylmethacrylate (I-A, C5). The resulting solution was spin coated onto a glass slide coated with indium tin oxide. The resulting film was dried 18 hours under nitrogen. The sample was placed in the poling apparatus so that it could be poled while monitoring the second harmonic signal which was generated. An electric field was applied and an SHG signal equal to approximately 80% of the maximum observed during the course of the poling process was observed within 10 min. The sample was then heated to 60° C. at a heating rate of approximately 1.0° C./min. The film was maintained at 60° C. for 10 min. to partially crosslink the film. The sample was then rapidly heated to 100° C. at a rate of 7° C./min. At this time the field was turned off and the SHG signal observed to fall to approximately 80% of its original value in a period of 1 min. The field was reapplied and the SHG signal restored to nearly the value it had before removal of the field. The sample was then heated at a rate of 2.0° C./min to 130° C. and held there 10 min. to complete the curing. It was then rapidly cooled to 100° C. and the field removed to determine if additional stability had occurred by heating to 130° C. The SHG signal was observed to fall by only 10% in a period similar to that which had resulted in a 20% decrease before the additional heating, indicating that additional crosslinking had taken place. The sample was then rapidly cooled to room temperature at which time the electric field was removed. When the field was removed the SHG signal decreased approximately 30% over a period of one day. After one day the SHG signal decreased at a rate of approximately 0.6%/day.

EXAMPLE 11

Polyisocyanatoethylmethacrylate - 2-amino-5-nitrophenol Network

The procedure of Example 5 for preparing crosslinked poled polymer was followed except that 0.02099 g (0.136 mmole) of crosslinking agent L (2-amino-5-nitrophenol) in 0.3 ml of tetrahydrofuran was used instead of the solution of crosslinking agent prepared in Example 5. The resulting solution was spin coated onto a glass slide coated with indium tin oxide. The resulting film was dried 23 hours under nitrogen. The sample was placed in the poling apparatus so that it could be poled while monitoring the second harmonic signal which was generated. An electric field was applied and an SHG signal equal to approximately 80% of the maximum observed during the course of the poling process was observed within 10 min. The sample was then heated to 60° C. at a heating rate of approximately 1.2° C./min. The film was maintained at 60° C. for 10 min. to partially crosslink the film. The sample was then heated at a rate of 1.0° C./min to 120° C. and held there 10 min. for further curing. The sample was then rapidly cooled to room temperature at which time the electric field was removed. When the field was removed the SHG signal decreased by approximately 20% over a period of two days. After two days the SHG signal was very stable, decreasing at a rate of 0.7%/day.

EXAMPLE 12

Polyisocyanatoethylmethacrylate - 4-Nitrocatechol Network

The procedure of Example 5 for preparing crosslinked poled polymer was followed except that 0.5 ml of a 10% solution of polyisocyanatoethylmethacrylate, prepared by procedure I-A, (Sample C5), and 0.0218 g (0.141 mmole) of crosslinking agent K (4-nitrocatechol) in 0.3 ml of tetrahydrofuran were used instead of the reagents described in Example 5. The resulting solution was spin coated onto a glass slide coated with indium tin oxide. The resulting film was dried 20 hours under nitrogen. The sample was placed in the poling apparatus so that it could be poled while monitoring the second harmonic signal which was generated. An electric field was applied and an SHG signal equal to approximately 75% of the maximum observed during the course of the poling process was observed within 10 min. The sample was then heated to 120° C. at a heating rate of approximately 0.8° C./min. The sample was heated at a uniform rate expcept for 10 min. pauses at 60° C., 80° C. and 100° C. These pauses were included in the heating procedure to partially crosslink the film. After reaching 120° C. the sample was held there 10 min. for further curing. The sample was then rapidly cooled to room temperature at which time the electric field was removed. When the field was removed the SHG signal decreased by approximately 25% over a period of four days. After four days the SHG signal was very stable, decreasing at a rate of 0.5%/day.

EXAMPLE 13

Poly(glycidyl methacrylate) - 2-amino-5-nitrophenol Network

The procedure of Example 5 for preparing crosslinked poled polymer was followed except that 0.02625 g (0.17 mmole) of crosslinking agent L (2-amino-5-nitrophenol) in 0.3 ml of tetrahydrofuran and 0.3 ml of a 20% by weight solution of poly(glycidyl methacrylate) in THF, prepared according to procedure I-B, were used. The resulting solution was spin coated onto a glass slide coated with indium tin oxide. The resulting film was dried 23 hours under nitrogen. The sample was placed in the poling apparatus so that it could be poled while monitoring the second harmonic signal which was generated. An electric field was applied and an SHG signal equal to approximately 5% of the maximum observed during the course of the poling process was observed within 10 min. The sample was then heated to 40° C. at a heating rate of approximately 1.0° C./min. during which time the SHG signal decreased by approximately 30%. The film was maintained at 40° C. for 10 min. to partially crosslink the film. The sample was then rapidly heated to 60° C. at a rate of 1° C./min. During this time the SHG signal was observed to decrease to essentially zero. The sample was then rapidly cooled back to room temperature. During the cooling the SHG signal was observed to increase to a value approximately twice that originally observed at room temperature. Since this behavior is usually indicative of sample conductivity and the larger final SHG signal gave evidence that some crosslinking had occurred which would decrease its conductivity, another attempt to pole the sample was made immediately. The sample was heated to 50° C. at a heating rate of 2.0° C./min. During the heating the SHG signal was observed to decrease more slowly than during the first poling attempt. The sample was then rapidly heated to 100° C. during which time the SHG signal fell to essentially zero. The sample was then maintained at 100° C. for 10 min. During this time the SHG signal was observed to start increasing indicating that the conductivity was reduced to the point where an internal field could be maintained. At the end of this 10 min. period the sample was rapidly cooled to room temperature. During the cooling the SHG signal increased to nearly the maximum value observed after the first attempt to pole the sample. The electric field was removed and the SHG signal was observed to decrease to about 30% of its maximum value within one day. After one day the SHG signal decreased at a rate of approximately 0.3%/day.

EXAMPLE 14

Poly(glycidyl methacrylate) - 4-nitrocatechol Network

The procedure of Example 5 for preparing crosslinked poled polymer was followed except that 0.0218 g (0.141 mmole) of crosslinking agent K (4-nitrocatechol) in 0.3 ml of tetrahydrofuran and 0.3 ml of a 20% by weight solution of poly(glycidyl methacrylate) in THF, prepared according to procedure I-A, (Sample B5) were used. The resulting solution was spin coated onto a glass slide coated with indium tin oxide. The resulting film was dried 92 hours under nitrogen. The sample was placed in the poling apparatus so that it could be poled while monitoring the second harmonic signal which was generated. An electric field was applied and an SHG signal equal to approximately 35% of the maximum observed during the course of the poling process was observed within 10 min. The sample was then heated to 90° C. at a heating rate of approximately 0.9° C./min. During this time the SHG signal was observed to decrease to essentially zero. The sample was then rapidly cooled back to room temperature. During the cooling the SHG signal was observed to increase to a value approximately twice that originally observed at room temperature. Measurement of the SHG signal with no field applied showed very little stability with the SHG signal decreasing to near zero in a period of ten minutes. Since the behavior exhibited during this portion of the poling process is usually indicative of sample conductivity and the larger final SHG signal gave evidence that some crosslinking had occurred which would decrease its conductivity, another attempt to pole the sample was made immediately. The sample was heated to 120° C. at a heating rate of 6.5° C./min. During the heating the SHG signal was Observed to decrease to zero. The sample was then maintained at 120° C. for 15 min. During this time the SHG signal was observed to start increasing indicating that the sample had been dried and crosslinked enough to reduce the conductivity to the point where an internal field could be maintained. At the end of this 15 min. period the sample was heated to 130° C. and maintained there another 15 min. to increase the rate of reaction. During this period the SHG signal was observed to increase to a value equal to 80% of the maximum value observed at any time during the experiment. The sample was then rapidly cooled to room temperature. During the cooling the SHG signal increased to nearly the maximum value observed after the first attempt to pole the sample. The electric field was removed and the SHG signal was observed to decrease to about 60% of its maximum value within one day. After one day the SHG signal decreased at a rate of approximately 0.1%/day.

EXAMPLE 15

Polyisocyanatoethylmethacrylate -

-continued

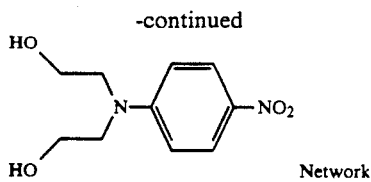

Network

A solution of 0.02603 g (0.115 mmoles) of crosslinking agent F, (HOCH$_2$CH$_2$)$_2$N-phenyl-NO$_2$, dissolved in 0.2 ml of THF was added to 0.4 ml of a 10% solution of the polyisocyanatoethyl methacrylate prepared according to procedure I-B in THF. The solution was spin coated on a glass slide the surface of which was made conductive by a layer of indium tin oxide. The film was then dried overnight under nitrogen. The film was placed in the electric field of the corona poling poling apparatus and slowly heated to 120° C. over a period of nine hours. The sample was maintained in the electric field at 120° C. for another nine hours at which time the temperature was then reduced to room temperature over period of one hour. The field was then removed. Subsequent measurements of the SHG signal showed that the induced nonlinear optical coefficient decreased approximately 10% over a two month time period. The measured d-coefficient was 1.67 pm/V one day after poling and 1.55 pm/V seven weeks later.

EXAMPLE 16

Polyisocyanatoethylmethacrylate -

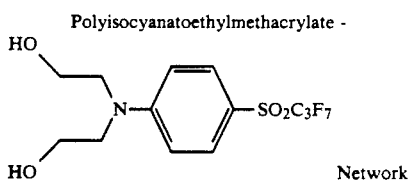

Network

A 10% by weight solution of polyisocyanatoethylmethacrylate prepared by procedure I-A (sample C5) was prepared in tetrahydrofuran. To 0.10 ml of this solution was added 0.0189 g (0.0458 mmole) of crosslinking agent G in 0.2 ml of tetrahydrofuran An additional 0.3 ml of tetrahydrofuran was added. The resulting solution was spin coated onto a glass slide coated with indium tin oxide. The resulting film was dried 23 hours under nitrogen. The sample was placed in the poling apparatus so that it could be poled while monitoring the second harmonic signal which was generated. An electric field was applied and an SHG signal equal to about 45% of the maximum observed during the course of the poling process was observed within 10 min. The sample was then heated to 60° C. at a heating rate of approximately 1.0° C./min. The film was maintained at 60° C. for 10 min. to partially crosslink the film. The sample was then heated to 75° C. at a rate of 1° C./min. The sample was then rapidly cooled to room temperature at which time the electric field was removed. When the field was removed the SHG signal decreased by a factor of 2.4 over a period of one day. After one day the SHG signal was much more stable, decreasing at a rate of about 2.9%/day.

EXAMPLE 17

Polyisocyanatoethylmethacrylate -

-continued

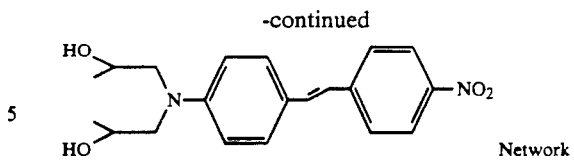

Network

A solution of 0.080 g (0.22 mmoles) of compound 1 dissolved in 1.2 ml of THF was added to 0.87 ml of a 10% solution of polymer C5 in THF. The solution was spin coated on a glass slide the surface of which was made conductive by a layer of indium tin oxide. The film was then dried in a vacuum oven at 50° C. for one hour, 120° C. for one hour and 150° C. for one hour. The film was placed in the electric field of a corona poling apparatus and slowly heated to 150° C. over a period of two hours. The sample was maintained in the electric field at 120° C. for another two hours at which time the temperature was then reduced to room temperature over a period of one-half hour. The field was then removed and the induced nonlinear optical coefficient was observed to decrease approximately 25% during the first ten minutes. In order to accelerate orientational relaxation, the sample was then maintained in a vacuum oven at 80° C. except during subsequent measurements of the induced nonlinearity. These measurements made over a period of approximately two months show essentially no change in the induced nonlinear optical coefficient.

EXAMPLE 18

Polyisocyanatoethylmethacrylate -

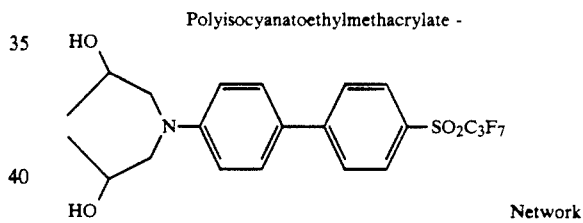

Network

A 10% by weight solution of polyisocyanatoethylmethacrylate prepared by procedure I-A (sample C5) was prepared in tetrahydrofuran. To 0.30 ml (0.1934 meq) of this solution was added 0.0177 g (0.0342 mmole) of crosslinking agent D in 0.2 ml of tetrahydrofuran. An additional 0.3 ml of tetrahydrofuran was added. The resulting solution was spin coated onto a glass slide coated with indium tin oxide. The resulting film was dried 28 hours under nitrogen. The sample was placed in the poling apparatus so that it could be poled while monitoring the second harmonic signal which was generated. An electric field was applied and an SHG signal equal to about 40% of the maximum observed during the course of the poling process was observed within 10 min. The sample was then heated to 60° C. at a heating rate of approximately 0.8° C./min. The film was maintained at 60° C. for 10 min. to partially crosslink the film. The sample was then heated to 100° C. at a rate of 1.3° C./min. The sample was then rapidly cooled to room temperature at which time the electric field was removed. When the field was removed the SHG signal decreased by a factor of two over a period of one day. After one day the SHG signal decreased at a rate of about 1.7%/day. Subsequent measurements showed essentially no signal, possibly as a result of laser damage.

EXAMPLE 19

Polyisocyanatoethylmethacrylate -

Network

A 10% by weight solution of polyisocyanatoethylmethacrylate prepared by procedure I-A (sample C5) was prepared in tetrahydrofuran. To 0.30 ml (0.1934 meq) of this solution was added 0.0329 g (0.069 mmole) of crosslinking agent C in 0.2 ml of tetrahydrofuran. An additional 0.3 ml of tetrahydrofuran was added. The resulting solution was spin coated onto a glass slide coated with indium tin oxide. The resulting film was dried 23 hours under nitrogen. The sample was placed in the poling apparatus so that it could be poled while monitoring the second harmonic signal which was generated. An electric field was applied and an SHG signal equal to about 50% of the maximum observed during the course of the poling process was observed within 10 min. The sample was then heated to 60° C. at a heating rate of approximately 1.1° C./min. The film was maintained at 60° C. for 10 min. to partially crosslink the film. The sample was then cooled to room temperature at which time the electric field was removed. When the field was removed the SHG signal decreased by a factor of five over a period of one day. After one day the SHG signal was very stable, decreasing at a rate of about 0.9%/day.

EXAMPLE 20

Polyisocyanatostyrene - 4-nitrocatechol Network

A 6.5% by weight solution of polyisocyanatostyrene prepared by procedure I-C (sample 1) was prepared in tetrahydrofuran. To 0.80 ml (0.359 meq) of this solution was added 0.040 g 0.0258 mmole) of crosslinking agent K, 4-nitrocatechol, in 0.2 ml of tetrahydrofuran. An additional 0.3 ml of tetrahydrofuran was added. The resulting solution was spin coated onto a glass slide coated with indium tin oxide. The resulting film was dried overnight under nitrogen. The sample was placed in the poling apparatus so that it could be poled while monitoring the second harmonic signal which was generated. An electric field was applied and an SHG signal equal to about 100% of the maximum observed during the course of the poling process was observed within 10 min. The sample was then heated to 100° C. at a heating rate of approximately 1.8° C./min. The film was maintained at 100° C. for 30 min. to crosslink the film. The sample was then rapidly cooled to room temperature at which time the electric field was removed. When the field was removed the SHG signal decreased to 28% of it starting value in a period of seven days. After seven days the SHG signal was decreased at a rate of about 1.3%/day.

EXAMPLE 21

Polyisocyanatostyrene - Disperse Red 19 Network

A 6.5% by weight solution of polyisocyanatostyrene prepared by procedure I-C (sample 1) was prepared in tetrahydrofuran. To 0.38 ml (0.170 meq) of this solution was added 0.040 g (0.0121 mmole) of crosslinking agent N, Disperse Red 19, in 0.2 ml of tetrahydrofuran. An additional 0.3 ml of tetrahydrofuran was added. The resulting solution was spin coated onto a glass slide coated with indium tin oxide. The resulting film was vacuum dried at 120° C. The high temperature drying was expected to partially crosslink the film. The sample was placed in the poling apparatus so that it could be poled while monitoring the second harmonic signal which was generated. An electric field was applied and an SHG signal equal to about 33% of the maximum observed during the course of the poling process was observed within 10 min. The sample was then heated to 150° C. at a heating rate of approximately 4.1° C./min. The field was turned off and the signal observed to decay to near zero in less than 10 minutes. The field was then reapplied and the SHG signal observed to return to the previous value. The sample was then heated to 180° C. and maintained there for 10min. It was then cooled to 170° C. and held there for 10 min. The sample was then cooled to 150° C. and the field turned off. The stability was observed to have dramatically improved with signal decreasing $\approx 65\%$ in a period of 20 minutes. The field was then reapplied and the sample then rapidly cooled to room temperature at which time the electric field was removed. When the field was removed the SHG signal decreased by $\approx 20\%$ in a period of one day. After one day the SHG signal was very stable, decreasing at a rate of about 1.4%/day.

EXAMPLE 22

Polyisocyanatostyrene -

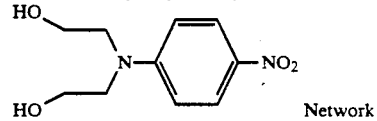

Network

A 6.5% by weight solution of polyisocyanatostyrene prepared by procedure I-C (sample 1) was prepared in tetrahydrofuran. To 0.79 ml (0.354 meq) of this solution was added 0.040 g (0.177 mmole) of crosslinking agent F in 0.2 ml of tetrahydrofuran. An additional 0.3 ml of tetrahydrofuran was added. The resulting solution was spin coated onto a glass slide coated with indium tin oxide. The resulting film was vacuum dried for one hour and then held under a vacuum overnight. The sample was placed in the poling apparatus so that it could be poled while monitoring the second harmonic signal which was generated. An electric field was applied and an SHG signal equal to about 6% of the maximum observed during the course of the poling process was observed within 10 min. The sample was then heated to 180° C. at a heating rate of approximately 6.0° C./min. The sample was maintained at 180° C. for 25 min. and then cooled to 150° C. The field was then turned off and the signal observed to decrease to 10% of its original value in 10 min. The field was reapplied and the sample cooled to 100° C. The field again was removed and the sample stability observed to have increased with $\approx 50\%$ of the signal still present after $\approx 20$ min. The field was then reapplied and the sample then rapidly cooled to room temperature at which time the electric field was removed. When the field was removed the SHG signal decreased at a rate of $\approx 7.7\%$/day.

EXAMPLE 23

Styrene - Isocyanatostyrene (2-1 copolymer) -

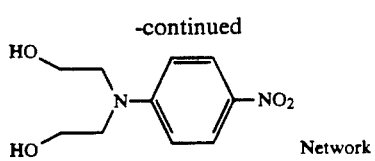
Network

A 10% by weight solution of polyisocyanatostyrene prepared by procedure I-C (sample 3) was prepared in tetrahydrofuran. To 0.62 ml (0.177 meq) of this solution was added 0.020 g (0.0884 mmole) of crosslinking agent F in 0.2 ml of tetrahydrofuran. An additional 0.3 ml of tetrahydrofuran was added. The resulting solution was spin coated onto a glass slide coated with indium tin oxide. The resulting film was dried at 150° C. for several hours under nitrogen. The sample was placed in the poling apparatus so that it could be poled while monitoring the second harmonic signal which was generated. An electric field was applied and an SHG signal equal to about 20% of the maximum observed during the course of the poling process was observed within 10 min. The sample was then heated to 180° C. at a heating rate of approximately 6.0° C./min. The sample was maintained at 180° C. for 25 min. and then cooled to 150° C. The field was then turned off and the signal observed to decrease to $\approx$1% of its original value in 20 min. The field was reapplied and the signal was observed to increase to $\approx$50% of the value present before the field was removed. The sample cooled to 100° C. The field again was removed and the sample stability observed to have increased with $\approx$50% of the signal still present after $\approx$40 min. The field was reapplied and the sample rapidly cooled to room temperature at which time the electric field was removed. When the field was removed the SHG signal decreased at a rate of $\approx$8.7%/day during the first six days. During the next 19 days it decreased at a rate of $\approx$1.6%/day.

EXAMPLE 24

Polyisocyanatoethylmethacrylate -

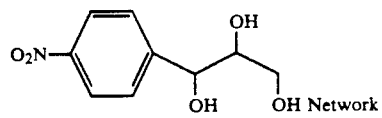
OH Network

A 10% by weight solution of polyisocyanatoethylmethacrylate prepared by procedure I-A (sample C5) was prepared in tetrahydrofuran. To 0.44 ml (0.28 meq) of this solution was added 0.030 g (0.141 mmole) of crosslinking agent H in 0.2 ml of tetrahydrofuran. An additional 0.3 ml of tetrahydrofuran was added. The resulting solution was spin coated onto a glass slide coated with indium tin oxide. The resulting film was vacuum dried at 50° C. overnight. It was then heated to 120° C. for 30 min and then 150° C. for 30 min. while under vacuum in order to partially crosslink the film. The sample was placed in the poling apparatus so that it could be poled while monitoring the second harmonic signal which was generated. An electric field was applied and an SHG signal equal to about 20% of the maximum observed during the course of the poling process was observed within 10 min. The sample was then heated to 180° C. at a heating rate of approximately 6.0° C./min. The film was maintained at 180° C. for 10 min. The sample was then rapidly cooled to room temperature at which time the electric field was removed.

When the field was removed the SHG signal decreased to 10% of its original value after 10 days.

EXAMPLE 25

Polyisocyanatoethylmethacrylate -

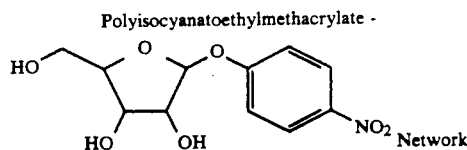
Network

A 10% by weight solution of polyisocyanatoethylmethacrylate prepared by procedure I-A (sample C5) was prepared in tetrahydrofuran. To 0.25 ml (0.162 meq) of this solution was added 0.022 g (0.0811 mmole) of crosslinking agent J in 0.2 ml of tetrahydrofuran. An additional 0.3 ml of tetrahydrofuran was added. The resulting solution was spin coated onto a glass slide coated with indium tin oxide. The resulting film was vacuum dried at 50° C. for 120 min and then at 100° C. for 30 min. in order to partially crosslink the film. The sample was placed in the poling apparatus so that it could be poled while monitoring the second harmonic signal which was generated. An electric field was applied and an SHG signal equal to about 50% of the maximum observed during the course of the poling process was observed within 10 min. The sample was then heated to 100° C. at a heating rate of approximately 5.0° C./min. The film was maintained at 100° C. for 10 min. to partially crosslink the film. The sample was then heated to 180° C. at a rate of 1.5° C./min. During this portion of the poling procedure the SHG signal was observed to decrease to 25% of its maximum value. The sample was then rapidly cooled to room temperature at which time the electric field was removed. When the field was removed the SHG signal decreased to 10% of its original value after three days.

From the foregoing description, one skilled in the art can easily ascertain the essential characteristics of this invention and, without departing from the spirit and scope thereof, can make various changes and modifications to the invention to adapt it to various usages and conditions.

What is claimed is:

1. A crosslinked polymer, comprising, the product of the reaction of:
   (a) a polymer reagent having a degree of polymerization of at least 3, and 2 or more active groups, said active groups being incapable of reacting with each other;
   (b) a crosslinking agent containing one or more dye moieties and two or more reactive groups; and
   wherein at least one of the polymer reagent or crosslinking agent has three or more active or reactive groups, respectively, and wherein said dye moiety has a molecular hyperpolarizability of greater than about $10^{-30}$ esu, and wherein the crosslinking agent is selected from the group consisting of [4-(2-hydroxmethyl-1-pyrrolidinyl)phenyl][1,1-difluoro-2-hydroxy-2-phenylethyl]sulfone, 1-[N,N-bis(2-hydroxyethyl)amino]-4-(2,2-dicyano-ethenyl)benzene, 3,3'-bis(hydroxymethyl)-4-N,N-dimethylamino-4'-nitro-trans-stilbene, 3,4-diaminonitrobenzene, 3,4-dihydroxynitrobenzene, 3-hydroxy-4-aminonitrobenzene, 4-bis(2-hydroxyethyl)aminonitrobenzene, a compound of the formula

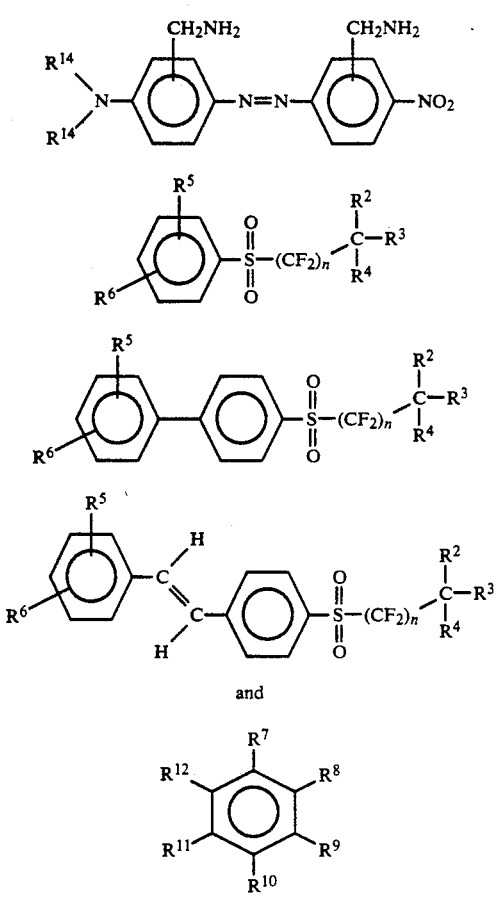

wherein:

R$^2$, R$^3$, R$^4$, R$^5$, and R$^6$ are independently selected from the group consisting of hydrogen, hydroxyl, amino, —OR$^{13}$, —NHR$^{13}$, hydroxyl or primary or secondary amino substituted hydrocarbyl of 1-20 carbon atoms, hydroxyl or primary or secondary amino substituted heterocyclic rings containing 3-6 carbon atoms, hydrocarbyl and heterocyclic rings containing 3-6 carbon atoms;

R$^{13}$ is hydroxyl or primary or secondary amino substituted hydrocarbyl of 1-20 carbon atoms, hydroxyl or primary or secondary amino substituted heterocyclic rings containing 3-6 carbon atoms, hydrocarbyl and heterocyclic rings containing 3-6 carbon atoms;

R$^7$, R$^8$, R$^9$, R$^{10}$, R$^{11}$, and R$^{12}$ are independently selected from the group consisting of hydrogen, hydroxyl, amino, —OR$^{13}$, —NHR$^{13}$, hydroxyl or primary or secondary amino substituted hydrocarbyl of 1-20 carbon atoms, hydroxyl or primary or secondary amino substituted heterocyclic rings containing 3-6 carbon atoms, hydrocarbyl and heterocyclic rings containing 3-6 carbon atoms;

R$^{14}$ is hydrocarbyl containing 1-20 carbon atoms; n is an integer of 1 to 20; and provided that at least two of R$^2$, R$^3$, R$^4$, R$^5$, R$^6$, R$^7$, R$^8$, R$^9$, R$^{10}$, R$^{11}$, R$^{12}$, and R$^{13}$ must be hydroxyl, amino, —OR$^{13}$, —NHR$^{13}$, hydroxyl or primary or secondary amino substituted hydrocarbyl of 1-20 carbon atoms, hydroxyl or primary or secondary amino substituted heterocyclic rings containing 3-6 carbon atoms, with the proviso that the dye moieties are aligned in conformance with an externally applied electric field.

2. The crosslinked polymer of claim 1 wherein the active groups are selected from the group consisting of epoxy, aziridinyl, isocyanate, acyl halide, carboxyl anhydride, and alkoxysilyl.

3. The croslinked polymer of claim 1 wherein the polymer reagent has at least about one active group for each two monomeric units.

4. The crosslinked polymer of claim 1 wherein the polymer reagent has at least about one active group for each three monomeric units.

5. The crosslinked polymer of claim 1 wherein the polymer reagent has a degree of polymerization of 5 to about 300.

6. The crosslinked polymer of claim 1 wherein polymer reagent has a degree of polymerization of about 10 to about 200.

7. The crosslinked polymer of claim 1 wherein the polymer reagent consists essentially of acrylic or styrenic monomers.

8. The crosslinked polymer of claim 1 wherein the active groups are selected from the group consisting of epoxy and isocyanate.

9. The crosslinked polymer of claim 1 wherein the active groups are selected from the group consisting of epoxy and isocyanate.

10. The crosslinked polymer of claim 9 wherein the polymer reagent has at least about one active group for each two monomeric units.

11. The crosslinked polymer of claim 10 wherein the polymer reagent has at least about one active group for each three monomeric units.

12. The crosslinked polymer of claim 10, wherein the crosslinking agent is selected from the group consisting of a compound of the formula

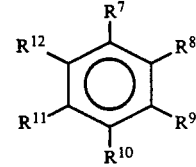

wherein at least two of R$^7$, R$^8$, R$^9$, R$^{10}$, R$^{11}$, and R$^{12}$ are independently selected from the group consisting of hydroxyl and amino, and one of R$^7$, R$^8$, R$^9$, R$^{10}$, R$^{11}$, and R$^{12}$ is nitro; 1-[N,N-bis(2-hydroxyethyl)amino]-4-(2,2-dicyanoethenyl)benzene; [4-(2-hydroxymethyl-1-pyrrolydinyl)phenyl][1,1,2,2,3,3,4,4-octafluoro-5-methyl-5-hydroxyhexyl]sulfone; and [4-(2-hydroxymethyl-1-pyrrolidinyl)phenyl][1,1-difluoro-2-hydroxy-2-phenylethyl]sulfone.

13. The crosslinked polymer of claim 12 wherein said crosslinking agent is selected from the group consisting of 3,4-diaminonitrobenzene, 3-hydroxy-4-aminonitrobenzene, 1-[N,N-bis(2-hydroxyethyl)amino]-4-(2,2-dicyanoethenyl)benzene, [4-(2-hydroxymethyl-1-pyrrolydinyl)phenyl][1,1,2,2,3,3,4,4-octafluoro-5-methyl-5-hydroxyhexyl]sulfone, and [4-(2-hydroxymethyl-1-pyrrolidinyl)phenyl][1,1-difluoro-2-hydroxy-2-phenylethyl]sulfone.

14. The process of claim 9 wherein the active groups are isocyanate.

15. The crosslinked polymer of claim 1 wherein the polymer reagent has a degree of polymerization of 5 to about 300.

16. The crosslinked polymer of claim 1 wherein the polymer reagent has a degree of polymerization of about 10 to about 200.

17. The crosslinked polymer of claim 1 wherein the polymer reagent consists essentially of acrylic or styrenic monomers.

18. The crosslinked polymer of claim 17 wherein the monomers are selected from the group consisting of acryloyl chloride, maleic anhydride, methacryloyl chloride, 2-isocyanatoethyl methacrylate, glycidyl methacrylate, glycidyl acrylate, 4-isocyanatostyrene, 3-(2-isocyanato-2-propyl)-α-methylstyrene, 2-hydroxymethyl methacrylate, 4-aminostyrene, methacrylic acid, 3-trimethoxysilylpropyl methacrylate, methyl methacrylate, styrene, 4-methylstyrene, cyclohexyl methacrylate, ethyl acrylate, and phenyl methacrylate.

19. The crosslinked polymer of claim 17 wherein the monomers are selected from the group consisting of acryloyl chloride, methacryloyl chloride, 2-isocyanatoethyl methacrylate, glycidyl methacrylate, glycidyl acrylate, 4-isocyanatostyrene, 3-(2-isocyanato-2-propyl)-α-methylstyrene, methyl methacrylate and styrene.

20. The crosslinked polymer of claim 1 wherein the crosslinking agent is selected from the group consisting of a compound of the formula

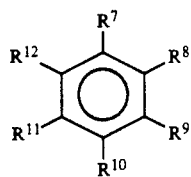

wherein: at least two of $R^7$, $R^8$, $R^9$, $R^{10}$, $R^{11}$, and $R^{12}$ are independently selected from the group consisting of hydroxyl and amino, and one of $R^7$, $R^8$, $R^9$, $R^{10}$, $R^{11}$, and $R^{12}$ is nitro; 1-[N,N-bis(2-hydroxyethyl)amino]-4-(2,2-dicyanoethenyl)benzene; [4-(2-hydroxymethyl-1-pyrrolydinyl)phenyl][1,1,2,2,3,3,4,4-octafluoro-5-methyl-5-hydroxyhexyl]sulfone; and [4-(2-hydroxymethyl-1-pyrrolidinyl)phenyl][1,1-difluoro-2-hydroxy-2-phenylethyl]sulfone.

21. The crosslinked polymer of claim 1 wherein said crosslinking agent is selected from the group consisting of 3,4-diaminonitrobenzene, 3-hydroxy-4-aminonitrobenzene, 1-[N,N-bis(2-hydroxyethyl)amino]-4-(2,2-dicyanoethenyl)benzene, [4-(2-hydroxymethyl-1-pyrrolydinyl)phenyl][1,1,2,2,3,3,4,4-octafluoro-5-methyl-5-hydroxyhexyl]sulfone, and [4-(2-hydroxymethyl-1-pyrrolidinyl)phenyl][1,1-difluoro-2-hydroxy-2-phenylethyl]sulfone.

22. A mixture, comprising,
(a) a polymer reagent having a degree of polymerization of at least 10, and 2 or more active groups, said active groups being incapable of reacting with each other; and
(b) a crosslinking agent containing one or more dye moieties and two or more reactive groups;
wherein at least one of the polymer reagent or crosslinking agent has three or more active or reactive groups respectively, and wherein said dye moiety has a molecular hyperpolarizability of greater than about $10^{-30}$ esu.

23. The mixture of claim 22 wherein the active or reactive groups are selected from the group consisting of epoxy, aziridinyl, isocyanate, acyl halide, carboxyl anhydride, and alkoxysilyl.

24. The mixture of claim 23 wherein the active or reactive groups are selected from the group consisting of epoxy and isocyanate.

25. The mixture of claim 22 wherein the polymer reagent has at least about one active group for each two monomeric units.

26. The mixture of claim 22 wherein the polymer reagent has a degree of polymerization of 5 to about 300.

27. The mixture of claim 22 wherein the polymer reagent has a degree of polymerization of about 10 to about 200.

28. The mixture of claim 22 wherein the polymer reagent consists essentially of acrylic or styrenic monomers.

29. The mixture of claim 28 wherein the monomers are selected from the group consisting of acryloyl chloride, maleic anhydride methacryloyl chloride, 2-isocyanatoethyl methacrylate, glycidyl methacrylate, glycidyl acrylate, 4-isocyanatostyrene, 3-(2-isocyanato-2-propyl)-α-methylstyrene, 2-hydroxyethyl methacrylate, 4-aminostyrene, methacrylic acid, 3-trimethoxysilylpropyl methacrylate, methyl methacrylate, styrene, 4-methylstyrene, cyclohexyl methacrylate, ethyl acrylate, and phenyl methacrylate.

30. The mixture of claim 22 wherein the crosslinking agent is selected from the group consisting of [4-(2-hydroxymethyl-1-pyrrolidinyl)phenyl]-(1,1-difluoro-2-hydroxy-2-phenylethyl]sulfone, 1-[N,N-bis(2-hydroxyethyl)amino]-4-(2,2-dicyanoethenyl)benzene, 3,3'-bis(hydroxymethyl)-4-N,N-dimethylamino-4'-nitro-transstilbene, 3,4-diaminonitrobenzene, 3,4-dihydroxynitrobenzene, 4-bis(2-hydroxyethyl)aminonitrobenzene, 3-hydroxy-4-aminonitrobenzene, a compound of the formula

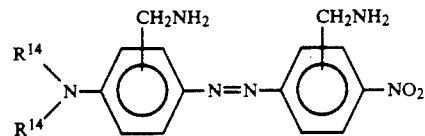

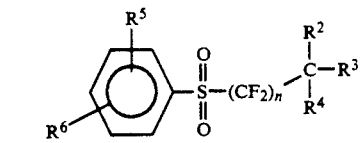

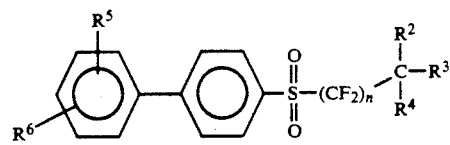

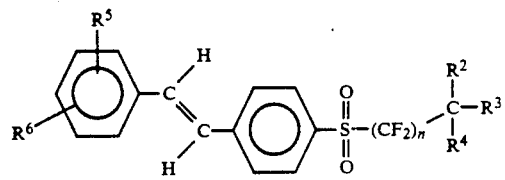

and

-continued

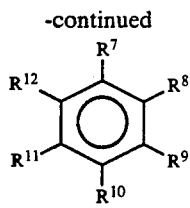

wherein:
$R^2$, $R^3$, $R^4$, $R^5$, and $R^6$ are independently selected from the group consisting of hydrogen, hydroxyl, amino, —$OR^{13}$, —$NHR^{13}$, hydroxyl or primary or secondary amino substituted hydrocarbyl of 1-20 carbon atoms, hydroxyl or primary or secondary amino substituted heterocyclic rings containing 3-6 carbon atoms, hydrocarbyl and heterocyclic rings containing 3-6 carbon atoms;

$R^{13}$ is hydroxyl or primary or secondary amino substituted hydrocarbyl of 1-20 carbon atoms, hydroxyl or primary or secondary amino substituted heterocyclic rings containing 3-6 carbon atoms, hydrocarbyl and heterocyclic rings containing 3-6 carbon atoms;

$R^7$, $R^8$, $R^9$, $R^{10}$, $R^{11}$, and $R^{12}$ are independently selected from the group consisting of hydrogen, hydroxyl, amino, —$OR^{13}$, —$NHR^{13}$, hydroxyl or primary or secondary amino substituted hydrocarbyl of 1-20 carbon atoms, hydroxyl or primary or secondary amino substituted heterocyclic rings containing 3-6 carbon atoms, hydrocarbyl and heterocyclic rings containing 3-6 carbon atoms;

$R^{14}$ is hydrocarbyl containing 1-20 carbon atoms;
n is an integer from 1 to 20; and
provided that at least two of $R^2$, $R^3$, $R^4$, $R^5$, $R^6$, $R^7$, $R^8$, $R^9$, $R^{10}$, $R^{11}$, $R^{12}$, and $R^{13}$ must be hydroxyl, amino, —$OR^{13}$, —$NHR^{13}$, hydroxyl or primary or secondary amino substituted hydrocarbyl of 1-20 carbon atoms, hydroxyl or primary or secondary amino substituted heterocyclic rings containing 3-6 carbon atoms.

31. A process for producing a crosslinked poled polymer, comprising:
crosslinking while simultaneously applying an electric field to, a mixture of;
(a) a polymer reagent having a degree of polymerization of at least 3, and 2 or more active groups, said active groups being incapable of reacting with each other; and
(b) a cross linking agent containing one or more dye moieties and two or more reactive groups;
wherein at least one of the polymer reagent or crosslinking agent has three or more active or reactive groups, respectively, and wherein said dye moiety has a molecular hyperpolarizability of greater than about $10^{-30}$ esu.

32. The process of claim 31 wherein the active or reactive groups are selected from the group consisting of epoxy, aziridinyl, isocyanate, acyl halide, carboxyl anhydride, and alkoxysilyl.

33. The process of of claim 32 wherein the active or reactive groups are selected from the group consisting of epoxy and isocyanate.

34. The process of claim 33 wherein the polymer reagent has at least about one active group for each two monomeric units.

35. The process of claim 34 wherein the polymer reagent has at least about one active group for each three monomeric units.

36. The process of claim 34 wherein the crosslinking agent is selected from the group consisting of [4-(2-hydroxymethyl-1-pyrrolidinyl)phenyl][1,1-difluoro-2-hydroxy-2-phenylethyl]sulfone, 1-[N,N-bis(2-hydroxyethyl)amino]-4-(2,2-dicyanoethenyl)benzene, 3,3'-bis(-hydroxymethyl)-4-N,N-dimethylamino-4'-nitro-transstilbene, 3,4-diaminonitrobenzene, 3,4-dihydroxynitrobenzene, 4-bis(2-hydroxyethyl)-aminonitrobenzene, 3-hydroxy-4-aminonitrobenzene, a compound of the formula

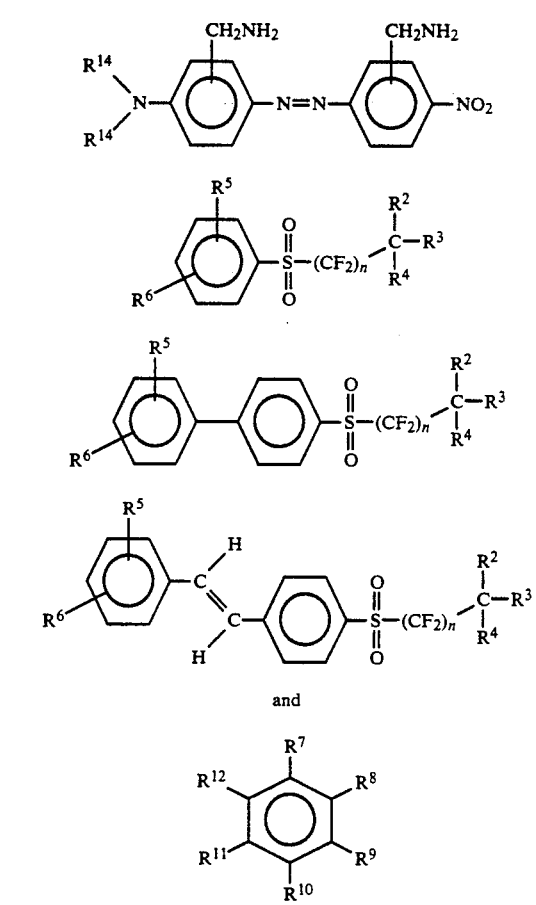

and wherein:
$R^2$, $R^3$, $R^4$, $R^5$, and $R^6$ are independently selected from the group consisting of hydrogen, hydroxyl, amino, —$OR^{13}$, —$NHR^{13}$, hydroxyl or primary or secondary amino substituted hydrocarbyl of 1-20 carbon atoms, hydroxyl or primary or secondary amino substituted heterocyclic rings containing 3-6 carbon atoms, hydrocarbyl and heterocyclic rings containing 3-6 carbon atoms;

$R^{13}$ is hydroxyl or primary or secondary amino substituted hydrocarbyl of 1-20 carbon atoms, hydroxyl or primary or secondary amino substituted heterocyclic rings containing 3-6 carbon atoms, hydrocarbyl and heterocyclic rings containing 3-6 carbon atoms;

$R^7$, $R^8$, $R^9$, $R^{10}$, $R^{11}$, and $R^{12}$ are independently selected from the group consisting of hydrogen, hydroxyl, amino, —$OR^{13}$, —$NHR^{13}$, hydroxyl or primary or secondary amino substituted hydrocarbyl of 1-20 carbon atoms, hydroxyl or primary or secondary amino substituted heterocyclic rings containing 3-6 carbon atoms, hydrocarbyl and heterocyclic rings containing 3-6 carbon atoms;

$R^{14}$ is hydrocarbyl containing 12-20 carbon atoms;

n is an integer from 1 to 20; and provided that at least two of $R^2$, $R^3$, $R^4$, $R^5$, $R^6$, $R^7$, $R^8$, $R^9$, $R^{10}$, $R^{11}$, $R^{12}$, and $R^{13}$ must be hydroxyl, amino, —$OR^{13}$, —$NHR^{13}$, hydroxyl or primary or secondary amino substituted hydrocarbyl of 1-20 carbon atoms, hydroxyl or primary or secondary amino substituted heterocyclic rings containing 3-6 carbon atoms.

37. The process of claim 36 wherein the crosslinking agent is selected from the group consisting of a compound of the formula

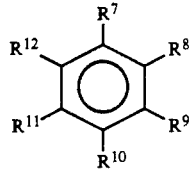

wherein: at least two of $R^7$, $R^8$, $R^9$, $R^{10}$, $R^{11}$, and $R^{12}$ are independently selected from the group consisting of hydroxyl and amino, and one of $R^7$, $R^8$, $R^9$, $R^{10}$, $R^{11}$, and $R^{12}$ is nitro; 1-[N,N-bis(2-hydroxyethyl)amino]-4-(2,2-dicyanoethenyl)benzene; [4-(2-hydroxymethyl-1-pyrrolydinyl)phenyl][1,1,2,2,3,3,4,4-octafluoro-5-methyl-5-hydroxyhexyl]sulfone; and [4-(2-hydroxymethyl-1-pyrrolidinyl)phenyl][1,1-difluoro-2-hydroxy-2-phenylethyl]sulfone.

38. The process of claim 33 wherein the active or reactive groups are isocyanate.

39. The process of claim 31 wherein the polymer reagent has at least about one active group for each two monomeric units.

40. The process of claim 31 wherein the polymer reagent has at least about one active group for each three monomeric units.

41. The process of claim 31 wherein the polymer reagent has a degree of polymerization of 5 to about 300.

42. The process of claim 31 wherein the polymer reagent has a degree of polymerization of about 10 to about 200.

43. The process of claim 31 wherein the polymer reagent consists essentially of acrylic or styrenic monomers.

44. The process of claim 43 wherein the monomers are selected from the group consisting of acryloyl chloride, maleic anhydride, methacryloyl chloride, 2-isocyanatoethyl methacrylate, glycidyl methacrylate, glycidyl acrylate, 4-isocyanatostyrene, 3-(2-isocyanato-2-2-propyl)-α-methylstyrene, 2-hydroxyethyl methacrylate, 4-aminostyrene, methacrylic acid, 3-trimethoxysilylpropyl methacrylate, methyl methacrylate, styrene, 4-methylstyrene, cyclohexyl methacrylate, ethyl acrylate, and phenyl methacrylate.

45. The process of claim 43 wherein the monomers are selected from the group consisting of acryloyl chloride, methacryloyl chloride, 2-isocyanatoethyl methacrylate, glycidyl methacrylate, glycidyl acrylate, 4-isocyanato-styrene, 3-(2-isocyanato-2-propyl)-α-methylstyrene, and methyl methacrylate and styrene.

46. The process of claim 31 wherein the crosslinking agent is selected from the group consisting of [4-(2-hydroxymethyl-1-pyrrolidinyl)phenyl]-[1,1-difluoro-2-hydroxy-2-phenylethyl]sulfone, 1-[N,N-bis(2-hydroxyethyl)amino]-4-(2,2-dicyanoethenyl)benzene, 3,3'-bis(-hydroxymethyl)-4-N,N-dimethylamino-4'-nitro-transstilbene, 3,4-diaminonitrobenzene, 3,4-dihydroxynitrobenzene, 4-bis(2-hydroxyethyl)-aminonitrobenzene, 3-hydroxy-4-aminonitrobenzene, a compound of the formula

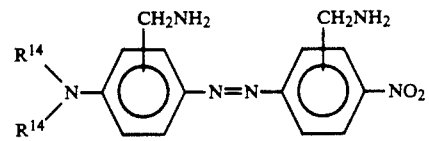

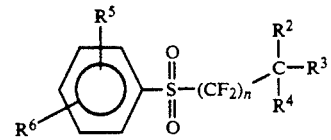

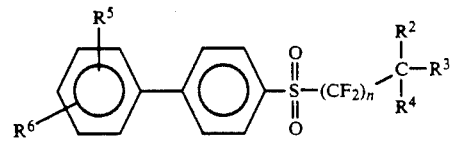

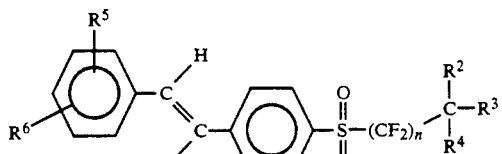

and

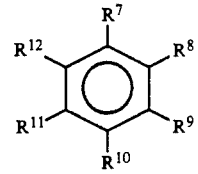

wherein:

$R^2$, $R^3$, $R^4$, $R^5$, and $R^6$ are independently selected from the group consisting of hydrogen, hydroxyl, amino, —$OR^{13}$, —$NHR^{13}$, hydroxyl or primary or secondary amino substituted hydrocarbyl of 1-20 carbon atoms, hydroxyl or primary or secondary amino substituted heterocyclic rings containing 3-6 carbon atoms, hydrocarbyl and heterocyclic rings containing 3-6 carbon atoms;

$R^{13}$ is hydroxyl or primary or secondary amino substituted hydrocarbyl of 1-20 carbon atoms, hydroxyl or primary or secondary amino substituted heterocyclic rings containing 3-6 carbon atoms, hydrocarbyl and heterocyclic rings containing 3-6 carbon atoms;

$R^7$, $R^8$, $R^9$, $R^{10}$, $R^{11}$, and $R^{12}$ are independently selected from the group consisting of hydrogen, hydroxyl, amino, —$OR^{13}$, —$NHR^{13}$, hydroxyl or primary or secondary amino substituted hydrocarbyl of 1-20 carbon atoms, hydroxyl or primary or secondary amino substituted heterocyclic rings containing 3-6 carbon atoms, hydrocarbyl and heterocyclic rings containing 3-6 carbon atoms;

R[14] is hydrocarbyl containing 12–20 carbon atoms;
n is an integer from 1 to 20; and
provided that at least two of R[2], R[3], R[4], R[5], R[6], R[7], R[8], R[9], R[10], R[11], R[12], and R[13] must be hydroxyl, amino, —OR[13], —NHR[13], hydroxyl or primary or secondary amino substituted hydrocarbyl of 1–20 carbon atoms, hydroxyl or primary or secondary amino substituted heterocyclic rings containing 3–6 carbon atoms.

47. The process of claim 46 wherein the crosslinking agent is selected from the group consisting of a compound of the formula

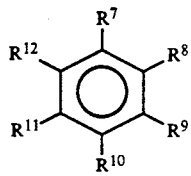

wherein: at least two of R[7], R[8], R[9], R[10], R[11], and R[12] are independently selected from the group consisting of hydroxyl and amino, and one of R[7], R[8], R[9], R[10], R[11], and R[12] is nitro; 1 -[N,N-bis(2-hydroxyethyl)amino]-4-(2,2-dicyanoethenyl)benzene; [4-(2-hydroxymethyl-1-pyrrolydinyl)phenyl][1,1,2,2,3,3,4,4-octafluoro-5-methyl-5-hydroxyhexyl]sulfone; and [4-(2-hydroxymethyl-1-pyrrolidinyl)phenyl][1,1-difluoro-2-hydroxy-2-phenylethyl]sulfone.

48. The process of claim 46 wherein the crosslinking agent is selected from the group consisting of 3,4-diaminonitrobenzene, 3-hydroxy-4-aminonitrobenzene, 1-[N,N-bis(2-hydroxyethyl)amino]-4-(2,2-dicyanoethenyl)-benzene, [4- 2-hydroxymethyl-1-pyrrolydinyl)-phenyl]-[1,1,2,2,3,3,4,4-octafluoro-5-methyl-5-hydroxyhexyl]-sulfone, and [4-(2-hydroxymethyl-1-pyrrolidinyl)-phenyl][1,1-difluoro-2-hydroxy-2-phenylethyl]sulfone.

49. The process of claim 31 carried out above the glass transition temperature of the mixture of the polymer reagent and the crosslinking agent.

50. A nonlinear optical device capable of second harmonic generation, comprising:
a nonlinear optical element, a source of coherent optical radiation, and means to direct the radiation emerging from the source into the nonlinear optical element, the nonlinear optical element comprising the product of the reaction of
(a) a polymer reagent having a degree of polymerization of at least 3, and 2 or more active groups, said active groups being incapable of reacting with each other; and
(b) a crosslinking agent containing one or more dye moieties and two or more reactive groups;
wherein at least one of the polymer reagent or crosslinking agent has three or more active or reactive groups, respectively, and the dye moieties are aligned in response to an externally applied electric field, and wherein said dye has a molecular hyperpolarizability of greater than about $10^{-30}$ esu.

51. The nonlinear optical device of claim 50 wherein the active or reactive groups are selected from the group consisting of epoxy, aziridinyl, isocyanate, acyl halide, carboxyl anhydride, and alkoxysilyl.

52. The nonlinear optical device of claim 50 wherein the polymer reagent has at least about one active group for each two monomeric units.

53. The nonlinear optical device of claim 50 wherein the polymer reagent has at least about one active group for each three monomeric units.

54. The nonlinear optical device of claim 50 wherein the polymer reagent has a degree of polymerization of 5 to about 300.

55. The nonlinear optical device of claim 50 wherein said polymer reagent has a degree of polymerization of about 10 to about 200.

56. The nonlinear optical element of claim 50 wherein the polymer reagent consists essentially of acrylic or styrenic monomers.

57. The nonlinear optical element of claim 56 wherein the monomers are selected from the group consisting of acryloyl chloride, maleic anhydride, methacryloyl chloride, 2-isocyanatoethyl methacrylate, glycidyl methacrylate, glycidyl acrylate, 4-isocyanatostyrene, 3-(2-isocyanato-2-propyl)-α-methylstyrene, 2-hydroxyethyl methacrylate, 4-aminostyrene, methacrylic acid, 3-trimethoxysilylpropyl methacrylate, methyl methacrylate, styrene, 4-methylstyrene, cyclohexyl methacrylate, ethyl acrylate, and phenyl methacrylate.

58. The nonlinear optical device of claim 56 wherein the monomers are selected from the group consisting of acryloyl chloride, methacryloyl chloride, 2-isocyanatoethyl methacrylate, glycidyl methacrylate, glycidyl acrylate 4-isocyanatostyrene, 3-(2-isocyanato-2-propyl)-α-methylstyrene, methyl methacrylate, and styrene.

59. The nonlinear optical element of claim 50 wherein the crosslinking agent is selected from the group consisting of [4-(2-hydroxymethyl-1-pyrrolidinyl)-phenyl][1,1-difluoro-2-hydroxy-2-phenylethyl]sulfone, 1-[N,N-bis(2-hydroxyethyl)amino]-4-(2,2-dicyanoethenyl)benzene, 3,3'-bis(hydroxymethyl)-4-N,N-dimethylamino-4'-nitro-trans-stilbene, 3,4-diamino-nitrobenzene, 3,4-dihydroxynitrobenzene, 4-bis(2-hydroxyethyl)aminonitrobenzene, 3-hydroxy-4-amino-nitrobenzene, a compound of the formula

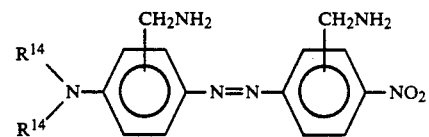

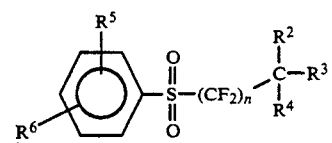

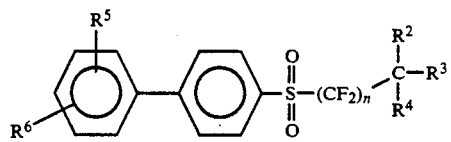

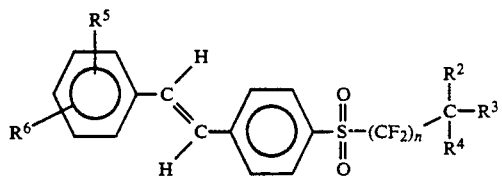

and

-continued

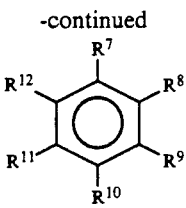

wherein:
- $R^2$, $R^3$, $R^4$, $R^5$, and $R^6$ are independently selected from the group consisting of hydrogen, hydroxyl, amino, —$OR^{13}$, —$NHR^{13}$, hydroxyl or primary or secondary amino substituted hydrocarbyl of 1-20 carbon atoms, hydroxyl or primary or secondary amino substituted heterocyclic rings containing 3-6 carbon atoms, hydrocarbyl and heterocyclic rings containing 3-6 carbon atoms;
- $R^{13}$ is hydroxyl or primary or secondary amino substituted hydrocarbyl of 1-20 carbon atoms, hydroxyl or primary or secondary amino substituted heterocyclic rings containing 3-6 carbon atoms, hydrocarbyl and heterocyclic rings containing 3-6 carbon atoms;
- $R^7$, $R^8$, $R^9$, $R^{10}$, $R^{11}$, and $R^{12}$ are independently selected from the group consisting of hydrogen, hydroxyl, amino, —$OR^{13}$, —$NHR^{13}$, hydroxyl or primary or secondary amino substituted hydrocarbyl of 1-20 carbon atoms, hydroxyl or primary or secondary amino substituted heterocyclic rings containing 3-6 carbon atoms, hydrocarbyl and heterocyclic rings containing 3-6 carbon atoms;
- n is an integer from 1 to 20; and
- provided that at least two of $R^2$, $R^3$, $R^4$, $R^5$, $R^6$, $R^7$, $R^8$, $R^9$, $R^{10}$, $R^{11}$, $R^{12}$, and $R^{13}$ must be hydroxyl, amino, —$OR^{13}$, —$NHR^{13}$, hydroxyl or primary or secondary amino substituted hydrocarbyl of 1-20 carbon atoms, hydroxyl or primary or secondary amino substituted heterocyclic rings containing 3-6 carbon atoms.

60. The nonlinear optical device of claim 59 wherein the crosslinking agent is selected from the group consisting of a compound of the formula

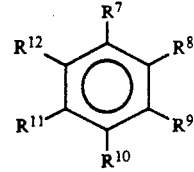

wherein: at least two of $R^7$, $R^8$, $R^9$, $R^{10}$, $R^{11}$, and $R^{12}$ are independently selected from the group consisting of hydroxyl and amino, and one of $R^7$, $R^8$, $R^9$, $R^{10}$, $R^{11}$, and $R^{12}$ is nitro; 1-[N,N-bis(2-hydroxyethyl)amino]-4-(2,2-dicyanoethenyl)benzene; [4-(2-hydroxymethyl-1-pyrrolydinyl)phenyl][1,1,2,2,3,3,4,4-octafluoro-5-methyl-5-hydroxyhexyl]sulfone; and [4-(2-hydroxymethyl-1-pyrrolidinyl)phenyl][1,1-difluoro-2-hydroxy-2-phenylethyl]sulfone.

61. The nonlinear optical device of claim 59 wherein the crosslinking agent is selected from the group consisting of 3,4-diaminonitrobenzene, 3-hydroxy-4-aminonitrobenzene, 1-[N,N-bis(2-hydroxyethyl)]-4-(2,2-dicyanoethenyl)benzene, [4-(2-hydroxymethyl-1-pyrrolydinyl)phenyl][1,1,2,2,3,3,4,4-octafluoro-5-methyl-5-hydroxyhexyl]sulfone, and[4-(2-hydroxymethyl-1-pyrrolidinyl)phenyl][1,1-difluoro-2-hydroxy-2-phenylethyl]sulfone.

* * * * *